US012708759B2

(12) United States Patent
Criscione et al.

(10) Patent No.: US 12,708,759 B2
(45) Date of Patent: Aug. 18, 2026

(54) CARDIAC COMPRESSION DEVICE HAVING PASSIVE AND ACTIVE CHAMBERS

(71) Applicants: THE TEXAS A&M UNIVERSITY SYSTEM, College Station, TX (US); CORINNOVA INCORPORATED, Houston, TX (US)

(72) Inventors: John C. Criscione, College Station, TX (US); Lewis D. Harrison, Flower Mound, TX (US); Michael R. Moreno, College Station, TX (US); Christina M. Bolch, Houston, TX (US); Dennis I. Robbins, Richardson, TX (US); Saurabh Biswas, College Station, TX (US); Boris Leschinsky, Mahwah, NJ (US)

(73) Assignees: Texas A&M University, College Station, TX (US); CorInnova Incoporated, Houston, TX (US)

( * ) Notice: Subject to any disclaimer, the term of this patent is extended or adjusted under 35 U.S.C. 154(b) by 291 days.

(21) Appl. No.: 17/861,581

(22) Filed: Jul. 11, 2022

(65) Prior Publication Data

US 2022/0346956 A1 Nov. 3, 2022

Related U.S. Application Data

(60) Division of application No. 15/365,223, filed on Nov. 30, 2016, now Pat. No. 11,511,102, which is a continuation-in-part of application No. 13/653,823, filed on Oct. 17, 2012, now Pat. No. 9,510,746.

(60) Provisional application No. 61/548,584, filed on Oct. 18, 2011.

(51) Int. Cl.

| | |
|---|---|
| *A61F 2/24* | (2006.01) |
| *A61M 60/148* | (2021.01) |
| *A61M 60/191* | (2021.01) |
| *A61M 60/268* | (2021.01) |
| *A61M 60/289* | (2021.01) |
| *A61M 60/468* | (2021.01) |
| *A61M 60/839* | (2021.01) |

(52) U.S. Cl.
CPC ......... *A61M 60/268* (2021.01); *A61F 2/2481* (2013.01); *A61M 60/148* (2021.01); *A61M 60/191* (2021.01); *A61M 60/289* (2021.01); *A61M 60/468* (2021.01); *A61M 60/839* (2021.01)

(58) Field of Classification Search
CPC .... A61F 2/0063; A61F 2/2478; A61F 2/2481; A61F 2002/0068–0072; A61F 2002/2484; A61F 2002/249; A61M 60/289
See application file for complete search history.

(56) References Cited

U.S. PATENT DOCUMENTS 2,826,193 A * 3/1958 Vineberg ........... A61M 60/839 601/153
3,513,836 A * 5/1970 Sausse ................ A61M 60/191 601/153

(Continued)

*Primary Examiner* — Eduardo C Robert
*Assistant Examiner* — Steven J Cotroneo
(74) *Attorney, Agent, or Firm* — Singleton Law, PLLC; Chainey P. Singleton

(57) ABSTRACT

The present invention provides methods, systems, kits, and cardiac compression devices that have both passive chambers and active chambers to improve heart function.

16 Claims, 15 Drawing Sheets

(56) References Cited

U.S. PATENT DOCUMENTS

| | | | | |
|---|---|---|---|---|
| 5,169,381 | A * | 12/1992 | Snyders | A61M 60/289 601/153 |
| 6,224,540 | B1 * | 5/2001 | Lederman | A61M 60/865 600/37 |
| 6,547,716 | B1 * | 4/2003 | Milbocker | A61M 60/191 600/37 |
| 7,468,029 | B1 * | 12/2008 | Robertson, Jr. | A61M 60/289 600/16 |
| 7,494,459 | B2 * | 2/2009 | Anstadt | A61M 60/531 600/17 |
| 8,944,986 | B2 * | 2/2015 | Altman | A61M 60/427 600/16 |
| 2005/0004420 | A1 * | 1/2005 | Criscione | A61F 2/2481 600/16 |
| 2008/0021260 | A1 * | 1/2008 | Criscione | A61M 60/191 600/16 |
| 2014/0194671 | A1 * | 7/2014 | Wildhirt | A61M 60/148 600/16 |

* cited by examiner

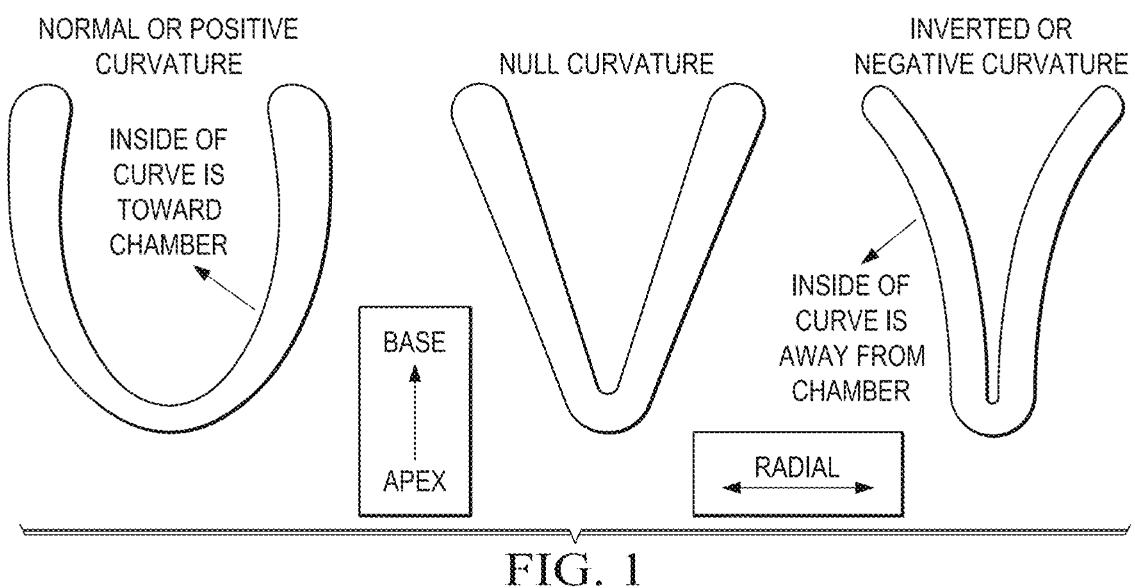
FIG. 1
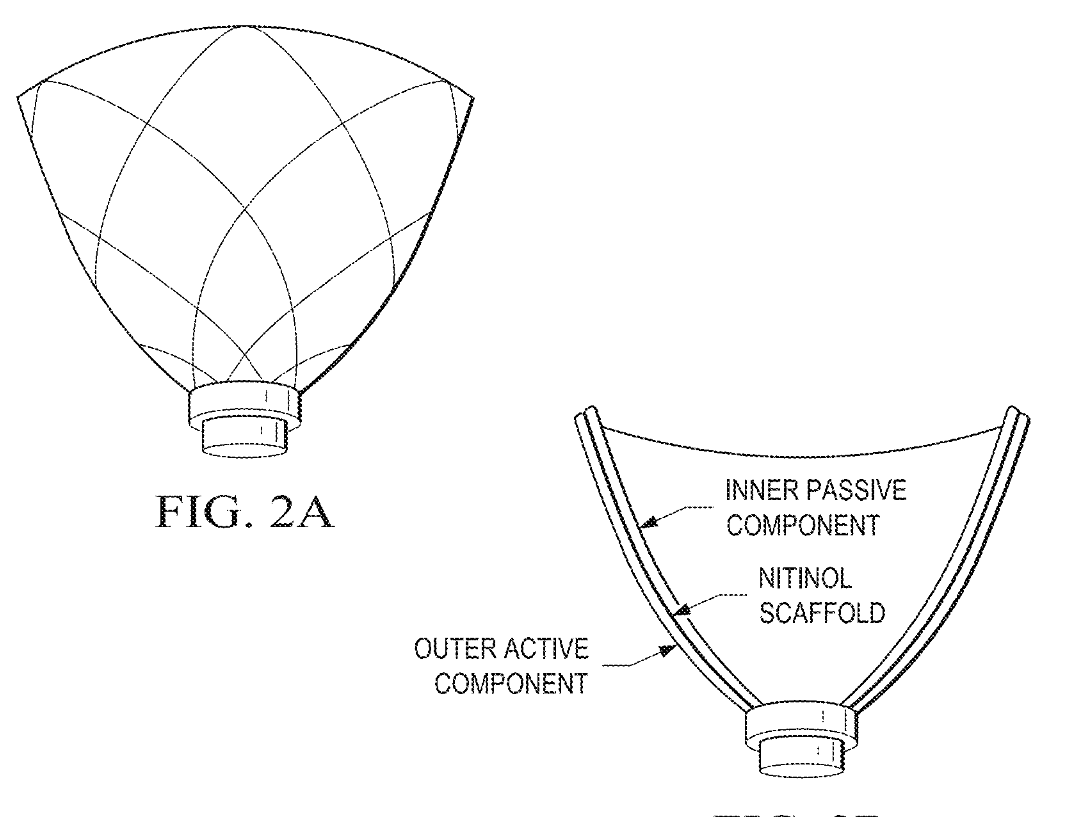
FIG. 2A
FIG. 2B

FIG. 12

FIG. 17A
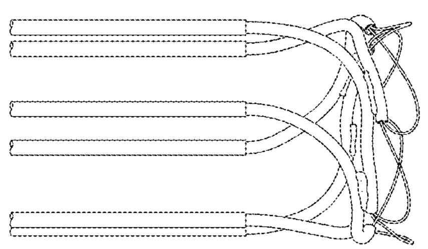
FIG. 17B
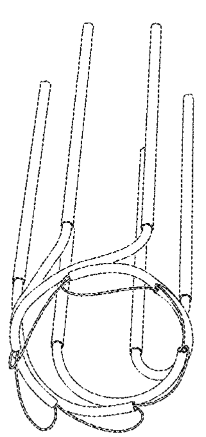
FIG. 17C
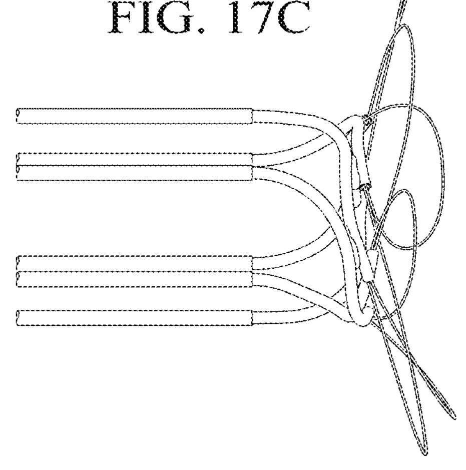
FIG. 17D
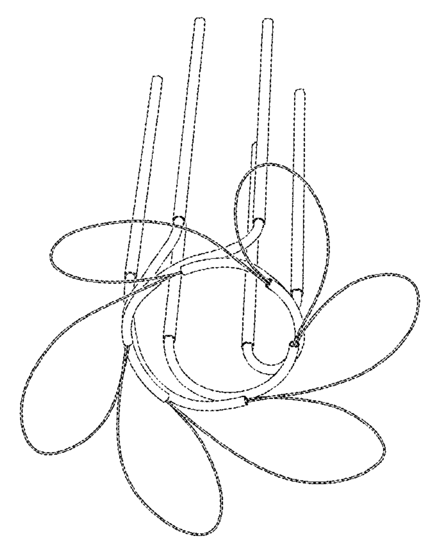
FIG. 18A
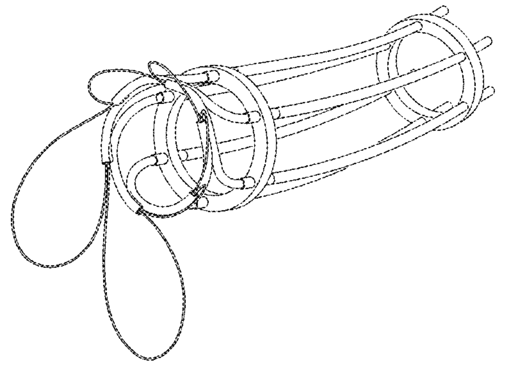
FIG. 18B

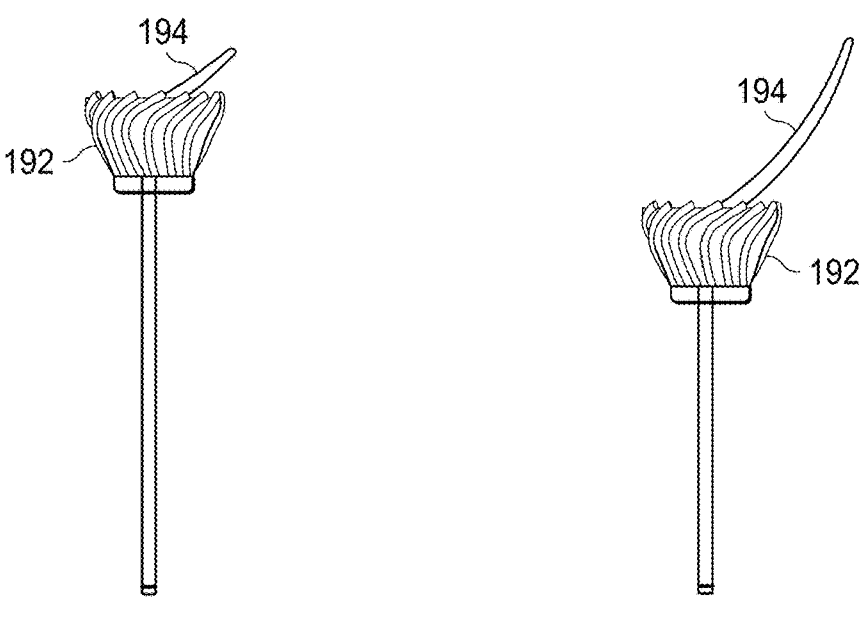
FIG. 19A
FIG. 19B
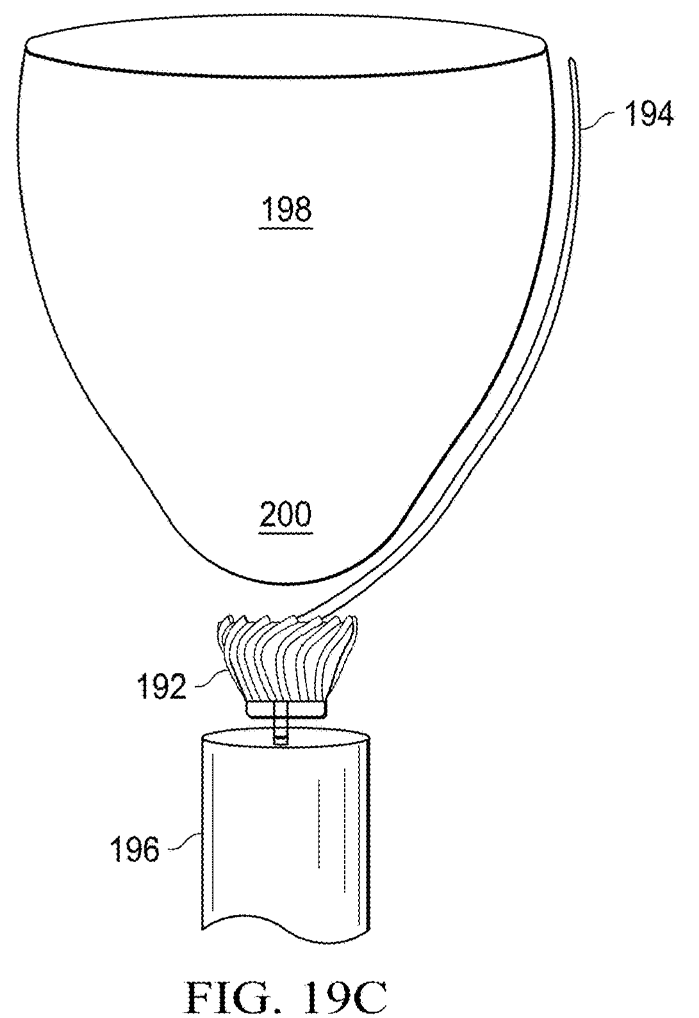
FIG. 19C

Passive Chamber Pressure (mmHg)

30
20
10
0
-10
-20
-30
-40

11:30:21 AM
11:30:22 AM
11:30:23 AM
11:30:24 AM

CARDIAC COMPRESSION DEVICE HAVING PASSIVE AND ACTIVE CHAMBERS

CROSS-REFERENCE TO RELATED APPLICATIONS

This application is a Divisional of U.S. patent application Ser. No. 15/635,223 filed Nov. 30, 2016, which is a Continuation-in-Part of U.S. patent application Ser. No. 13/653,823 filed Oct. 17, 2012, now U.S. Pat. No. 9,510,746, which claims priority to U.S. Provisional Patent Application Ser. No. 61/548,584 filed Oct. 18, 2011, now expired, and is related to U.S. patent application Ser. No. 11/400,148 filed Apr. 6, 2006, now U.S. Pat. No. 7,935,045, which claims priority to U.S. Provisional Patent Application Ser. No. 60/668,640 filed Apr. 6, 2005, now expired, and is related to U.S. patent application Ser. No. 10/870,619 filed Jun. 17, 2004, now U.S. Pat. No. 7,445,593, the contents of which are all incorporated by reference herein in their entirety.

STATEMENT OF FEDERALLY FUNDED RESEARCH

This invention was made with U.S. Government support under Contract Nos. 1 R42 HL080759-01 and 4 R42 HL080759-02 awarded by the NIH and Contract No. IIP-0912711 awarded by the NSF. The government has certain rights in this invention.

TECHNICAL FIELD OF THE INVENTION

The present invention relates in general to a mechanical interface for the heart of a patient to improve its pumping function, and, more particularly, modulate contraction strain patterns on a diseased or damaged heart in order to reduce dyskinetic or hypokinetic motions.

BACKGROUND OF THE INVENTION

Congestive heart failure (CHF) is a debilitating disease that is generally initiated by some index cardiac event that results in muscle damage and a decline in cardiac pumping ability. The precipitating index event may be episodic, occurring abruptly, e.g., myocardial infarction; or it may develop gradually over time, e.g., genetic cardiomyopathy. Following the index event, a decline in pumping capacity triggers neurohormonal compensatory mechanisms, which are activated to restore and maintain healthy cardiac output. Due to the effectiveness of these compensatory mechanisms, it is often difficult to recognize the development of persistent underlying disease, as the patient may appear asymptomatic with respect to metrics such as ejection fraction and cardiac output. Nevertheless, evidence of disease may be physically present in the aberrant motion and subsequent remodeling of the failing heart. Left ventricular (LV) remodeling is a progressive phenomenon characterized globally by remodeling of LV chamber size and shape, with a corresponding loss of cardiomyocytes, myocyte hypertrophy and interstitial fibrosis. Left ventricular remodeling dramatically alters the mechanical environment, which in turn influences growth and remodeling processes. It is well established that mechanical stimuli (e.g., stress or strain) are important epigenetic factors in cardiovascular development, adaptation, and disease. Changes in heart structure and function result in changes in the mechanical forces sensed by the cells. This alters the biochemical activity of the cells, which in turn stimulates changes in the structure and function of the heart. Interestingly, abnormal cardiac kinematics is often considered a symptom of heart failure when in actuality it is likely that aberrant motion is a primary contributing factor to the aberrant growth and remodeling i.e., cellular responses to the pathologic mechanical factors lead to further pathologic remodeling and a positive feedback loop emerges such that eventually a threshold is reached wherein the neurohormonal compensatory mechanisms activated to maintain homeostasis are no longer sufficient to deter further progression of the disease. Consequently, treatment strategies that fail to remedy the aberrant mechanical environment become increasingly ineffective as the disease progresses.

There are numerous cardiac devices, artificial hearts, and heart assist devices currently on the market. In addition, there are other therapies like drugs, biventricular pacing, stem cell therapies, blood contacting assist devices, surgical manipulations, or passive stents, and constraints which typically off-load the heart, and thus, only modulate the strain pattern indirectly.

One heart assist device is shown in U.S. Pat. No. 5,119,804, issued on Jun. 9, 1992 to Anstadt, for a cardiac massage apparatus and a drive system. The cardiac massage apparatus includes a cup having a liner that is connected within the cup at its upper and lower ends. Dimensions defining an optimum cup shape as a function of ventricular length are disclosed wherein the heart remains within the cup when mechanically activated.

Other examples include U.S. Pat. Nos. 6,663,558; 6,612,979; 6,612,978; 6,602,184; and 6,595,912, issued to Lau et al., for a cardiac harness to treat congestive heart failure. The harness applies elastic, compressive reinforcement on the LV to reduce deleterious wall tension and to resist shape change of the ventricle during the mechanical cardiac cycle. Rather than imposing a dimension beyond which the heart cannot expand, the harness provides no hard limit over the range of diastolic expansion of the ventricle. Instead, the harness follows the contour of the heart throughout diastole and continuously exerts gentle resistance to stretch.

U.S. Pat. No. 6,602,182, issued on Aug. 5, 2003, to Milbocker, for a unified, non-blood contacting, implantable heart assist system surrounds the natural heart and provides circumferential contraction in synchrony with the heart's natural contractions. The pumping unit includes adjacent tube pairs arranged along a bias with respect to the axis of the heart and bound in a non-distensible sheath forming a heart wrap. The tube pairs are tapered at both ends such that when they are juxtaposed and deflated they approximately follow the surface of the diastolic myocardium. Inflation of the tube pairs causes the wrap to follow the motion of the myocardial surface during systole. A muscle-driven or electromagnetically powered energy converter inflates the tubes using hydraulic fluid pressure. An implanted electronic controller detects electrical activity in the natural heart, synchronizes pumping activity with this signal, and measures and diagnoses system as well as physiological operating parameters for automated operation. A transcutaneous energy transmission and telemetry subsystem allows the Unified System to be controlled and powered externally.

U.S. Pat. No. 6,592,619, issued on Jul. 15, 2003 to Melvin, for an actuation system for assisting the operation of the natural heart. The system includes a framework for interfacing with a natural heart, through the wall of the heart, which includes an internal framework element configured to be positioned within the interior volume of a heart and an external framework element configured to be positioned proximate an exterior surface of the heart. The internal framework is flexibly suspended with respect to the external frame. An actuator system is coupled to the framework and configured to engage an exterior surface of the heart. The actuator system includes an actuator band extending along a portion of a heart wall exterior surface. The actuator band is selectively movable between an actuated state and a relaxed state and is operable, when in the actuated state, to assume a predetermined shape and thereby indent a portion of the heart wall to affect a reduction in the volume of the heart. A drive apparatus is coupled to the actuator band and is operable for selectively moving the actuator band between the relaxed and actuated states to achieve the desired assistance of the natural heart.

U.S. Pat. No. 6,224,540, issued on May 1, 2001, to Lederman et al., relates to a passive girdle for heart ventricle for therapeutic aid to patients having ventricular dilatation. A passive girdle is wrapped around a heart muscle which has dilatation of a ventricle to conform to the size and shape of the heart and to constrain the dilatation during diastole. The girdle is formed of a material and structure that does not expand away from the heart but may, over an extended period of time be decreased in size as dilatation decreases.

The foregoing problems have been recognized for many years and while numerous solutions have been proposed, none of them adequately address all of the problems.

SUMMARY OF THE INVENTION

The present invention provides a Direct Cardiac Compression Device (DCCD) adapted to surround the heart and comprising an inner passive chamber comprising an inner membrane adapted to surround the heart, a connecting membrane in communication with the inner membrane, one or more passive dividers located between the inner membrane and the connecting membrane to form inner passive chambers, and a passive fluid deposited in the inner passive chambers, wherein the inner passive chambers conform to the shape of the heart; an outer active chamber comprising an outer member in communication with the connecting membrane, one or more active dividers located between the outer member and the connecting membrane to form outer active chambers, and an active fluid disposed in the outer active chamber; an input connection in fluid communication with the outer active chamber to ingress the active fluid into the outer active chamber, and an output connection in fluid communication with the outer active chamber to egress the fluid from the outer active chamber, wherein the active fluid presses on the inner passive chambers to compress the heart.

The present invention provides a Direct Cardiac Compression Device adapted to surround the heart and comprising an inner passive chamber comprising an inner membrane adapted to surround the heart, a connecting membrane in communication with the inner membrane to form an inner passive chamber, and a passive fluid deposited in the inner passive chamber; an outer active chamber comprising an outer member in communication with the connecting membrane to form an outer active chamber, and an active fluid disposed in the outer active chamber; an input connection in fluid communication with the outer active chamber to ingress the active fluid into the outer active chamber, and an output connection in fluid communication with the outer active chamber to egress the fluid from the outer active chamber.

The device may further include a pneumatic driver operably linked to the input connection to pressurize the outer active chamber to compress the heart and to the output connection to depressurize the outer active chamber. The passive fluid may or may not change in volume depending on the desired application. The volume may be set prior to insertion through a port or be in various volumes. The passive fluid may be a liquid, a gas, a gel, or a polymer. The passive fluid may be saline. Similarly, the active fluid may be a gas.

The device of claim may further include one or more inner passive dividers positioned between the inner passive membrane and the connecting membrane to form 2 or more passive chambers, e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, or more. In addition, these inner passive dividers may be positioned horizontally, vertically or both as well as in a series of spiral lines extending from the hub of the device. Such spirals may be designed to be clock-wise (looking down the hub) so as to complement the strain pattern of the heart muscle and allow the heart apex to naturally twist during systolic contraction. Similarly, each inner passive chamber may have a connection to one or more of the adjacent inner passive chambers to equalize volumes.

Similarly, the device may further include one or more active dividers positioned between the outer member and the connecting membrane to form 2 or more active chambers, e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, or more. In addition, these inner active dividers may be positioned horizontally, vertically, form one or more spirals, etc. Similarly, each active chamber may have a connection to one or more of the adjacent active chambers to equalize volumes.

In some embodiments, the inner passive membrane may be contoured to surround the heart operable to actively promote a contraction strain pattern characterized by non-inversion or lack of gross perturbation of the curvature on a diseased or damaged myocardium that promotes beneficial growth and remodeling of the myocardium. The device may exert a non curvature-inverting contraction stain pattern when used on a heart, when the fluid is pressurized. The device may further include a shell surrounding the outer member. The device applies varying pressure, uniform pressure or both to the surface of the heart to alter an end-systolic configuration of the heart, an end-diastolic configuration of the heart, or both.

The device may further include one or more components designed to provide adjustable passive support, active assist, or a combination of active assist and passive support to a damaged or diseased heart. The inner membrane may be adapted to form a pneumatic lock with the heart surface making it difficult to dislodge the device in the absence of outside air ingress. The device may further include one or more structural elements disposed about the direct cardiac compression device.

The present invention provides a method to improve diastolic recoil of a heart using a direct cardiac contact compression device comprising the steps of: providing a direct cardiac compression device, wherein the direct cardiac compression device comprises an inner passive chamber comprising an inner membrane adapted to surround the heart, a connecting membrane in communication with the inner membrane, one or more passive dividers located between the inner membrane and the connecting membrane to form inner passive chambers, and a passive fluid deposited in the inner passive chambers, wherein the inner passive chambers conform to the shape of the heart; an outer active chamber comprising an outer member in communication with the connecting membrane, one or more active dividers located between the outer member and the connecting membrane to form outer active chambers, and an active fluid disposed in the outer active chamber; an input connection in fluid communication with the outer active chamber to ingress the active fluid into the outer active chamber, and an output connection in fluid communication with the outer active chamber to egress the fluid from the outer active chamber, wherein the active fluid presses on the inner passive chambers to compress the heart; implanting the direct cardiac compression device around a heart; pressurizing the outer active chamber to expand the outer active chamber; applying force to the inner passive chamber to compress the inner membrane which selectively compresses the heart; depressurize the outer active chamber during recoil to contract the inner passive chamber and move the inner membrane away from the heart.

The method may further include the step of connecting a pneumatic driver to the input connection and the output connection to pressurize the outer active chamber to compress the heart and depressurize the outer active chamber to aid in filling the heart.

The method may further include a passive port in communication with the passive fluid to adjust a passive fluid volume and further comprising the step of adjusting a volume of the passive fluid.

BRIEF DESCRIPTION OF THE DRAWINGS

For a more complete understanding of the features and advantages of the present invention, reference is now made to the detailed description of the invention along with the accompanying figures and in which:

FIG. 1 is an image of a normal, a null, and an inverted curvature in apex-to-base, radial plane (long axis);

FIG. 2A is an image depicting the geometry and orientation of the Nitinol Scaffold.

FIG. 2B is a cross sectional image of the device revealing the inner passive component, the outer active component and the location of the Nitinol Scaffold between these two components;

FIG. 9A is an image of the inner passive component of the device conforming to the heart during end-diastolic configuration, whereas

FIG. 12 is an image of the pressure-volume loops of the left ventricle prior to device deployment and after deployment;

FIGS. 17A-17D are images of the pericardial stabilizer. FIG. 17A is an image of a side view of the pericardial stabilizer with nitinol wire loops retracted. FIG. 17B is an image of a front view of the pericardial stabilizer with nitinol wire loops retracted.

FIG. 17C is an image of a side view of the stabilizer with nitinol loops expanded. FIG. 17D is an image of a front view of the stabilizer with nitinol loops expanded;

FIG. 18A is an image that shows the pericardial stabilizer with two of the six wire loops deployed and FIG. 18B is an image that shows the longitudinal curvature of the pericardial stabilizer; and FIGS. 19A-19C are images that shows one embodiment of the sliding hub of the present invention.

FIG. 21A shows the pressure inside the device at initial insertion FIG. 21A, FIG. 21B shows the pressure inside the device during normal operation and FIG. 21C shows the pressure inside the device to maintain a positive pressure in the passive chambers for as much of a systolic duration as possible.

DETAILED DESCRIPTION OF THE INVENTION

Figure 3:
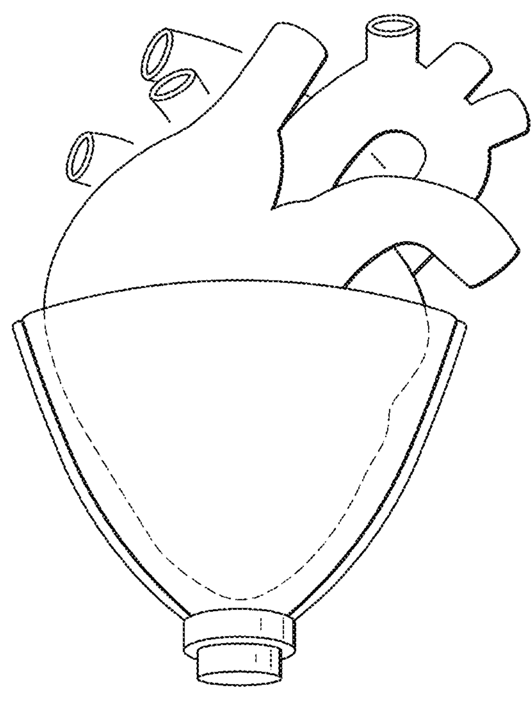
FIG. 3 is an image depicting the inner passive component bladder filled with saline via a subcutaneous injection port that conforms to the shape of the heart and can therefore be used to fit the device to the heart and/or provide adjustable passive support or constraint.

While the making and using of various embodiments of the present invention are discussed in detail below, it should be appreciated that the present invention provides many applicable inventive concepts that can be embodied in a wide variety of specific contexts.

The terminology used and specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the "cardiac rekinesis therapy" is the restoration of physiological or beneficial motion to the heart, or in other words, to eliminate aberrant or pathophysiological motions or strains, as opposed to circulatory assist therapies.

As used herein, a "biomedical material" is a material, which is physiologically inert to avoid rejection or other negative inflammatory response.

One of the major maladaptive changes after a major heart attack or cardiac event is an initial decline in pumping capacity of the heart leading to activation of a variety of compensatory mechanisms, and subsequently a phenomenon known as cardiac or left ventricular remodeling, i.e., a geometrical change in the architecture of the left ventricle. Evidence suggests that the local mechanical environment governs remodeling processes. Thus, in order to control two important mechanical parameters, cardiac size and cardiac output, we have developed a minimally invasive direct cardiac contact device capable of providing two actions simultaneously: (1) adjustable cardiac support to modulate cardiac size and (2) synchronous active assist to modulate cardiac output and correct motion. As a means of determining the role of these mechanical parameters in reverse remodeling or ventricular recovery, the device was further designed to (1) be deployed via minimally invasive surgical procedures; (2) allow uninhibited motion of the heart; (3) remain in place about the heart via an intrinsic pneumatic attachment; and (4) provide direct cardiac compression without aberrantly inverting the curvature of the heart. These actions and features are mapped to particular design solutions and assessed in an acute implantation in an ovine model of acute heart failure (esmolol overdose). The passive support component was used to effectively shift the EDPVR leftward, i.e., counter to the effects of disease. The active assist component was used to effectively decompress the constrained heart and restore lost cardiac output and stroke work in the esmolol failure model. It is expected that such a device will provide better control of the mechanical environment and thereby provide cardiac surgeons a broader range of therapeutic options and unique intervention possibilities.

Given the prominent role of mechanical factors in driving the remodeling associated with disease progression, the authors sought an implantable device to directly modulate heart size and motion; so to investigate the effectiveness of mechanical therapy designed to guide potential restorative-remodeling processes. The device surrounds the heart, contacts the epicardial surface of the heart, and thus acts on the heart directly, without blood contact.

The following modes of operation or device-mediated actions include modes of operation implemented independently or simultaneously, and include: (A1) adjustable cardiac support or passive constraint to reduce heart size and (A2) synchronous active assist to correct and increase heart motion or stroke volume, stroke work, ejection fraction, and/or cardiac output.

The device of the present invention also provides: (F1) delivery and deployment via minimally invasive surgical procedures; (F2) does not impede heart function when device is inactive (i.e., nonobligatory); (F3) does not invert heart curvature (nor induce similar, abnormal motions) when it is activated; and (F4) does not dislodge, extrude or expel the heart when it is activated.

There is a recent report of a device capable of adjustable cardiac support and there are reports of a direct cardiac compression device for providing synchronous active assist. However, there is not a device capable of adjustable cardiac support or passive constraint to reduce heart size and synchronous active assist to correct and increase heart motion or stroke volume, stroke work, ejection fraction, and/or cardiac output. Existing direct cardiac compression devices, moreover, are designed to increase ejection fraction. This is in contrast to the device of the present invention described herein, which is designed to maintain and/or restore normal cardiac kinematics. This is an important distinction as existing direct cardiac compression devices are typically designed to invert curvature as a means of increasing ejection fraction. The resulting aberrant strain patterns are not conducive to restorative remodeling. Conversely, the present invention provides a device that is designed to restore and/or maintain a healthy mechanical environment and improvements in cardiac output, while maintaining mechanical conditions conducive for potential restorative remodeling processes to occur.

FIG. 1 is an image of a normal, a null, and an inverted curvature in apex-to-base, radial plane (long axis). Direct cardiac compression devices designed to invert the curvature of the heart to increase ejection fraction are inducing aberrant strain patterns that are not likely conducive to restorative remodeling processes and/or cardiac rehabilitation. The device implanted was a soft compliant cup shaped device with an inner passive layer containing six fluid chambers and an outer active layer containing six fluid chambers. The chambers were composed of a thin nylon film and mounted on a nitinol wire scaffold, which provided structural stability.

FIG. 2A is an image depicting the geometry and orientation of the Nitinol scaffold. FIG. 2B is a cross sectional image of the device revealing the inner passive component, the outer active component and the location of the Nitinol scaffold between these two components. Each chamber had an identical helical orientation, but shifted 60 degrees so to form a complete circumference as a cup-shaped structure. The inner and outer layers were offset such that the seams between the chambers did not overlap. Saline was the working fluid for the inner passive chambers and air was the working fluid for the outer active chambers. The saline filled passive chambers allowed the device to be fit to the heart with or without providing support and/or constraint.

FIG. 3 is an image depicting the inner passive component bladder filled with saline via a subcutaneous injection port it conforms to the shape of the heart and can therefore be used to fit the device to the heart and/or provide adjustable passive support or constraint. Polyurethane tubing (0.25 inches diameter) was employed as the conduit for air transport to and from the active chambers. The end of the tubing within the active chambers was spiral cut to prevent the nylon film from collapsing onto the tube end during the diastolic phase of assist, when vacuum was applied to remove air from the chambers. The other tube ends were coalesced together into a single driveline (0.375 inches diameter). Smaller diameter tubing (0.125 inches diameter) was use for the passive chambers and coalesced into a single driveline that was subsequently fitted onto the male adapter of a standard three-way valve for saline infusion with a syringe. Although separate in construction, tubing connections made the six-chambers of a given (inner passive or outer active) layer contiguous with the same pressure source.

The device pressure was monitored continuously via use of a Millar pressure catheter transducer (Millar Instruments Inc., Houston, Tex.) placed within one of the inner passive chambers. The nitinol wire scaffold served as a reference electrode for acquisition of the ECG signal used to trigger the device. The sense electrode was sewn to the heart apex. This epicardial electrode configuration provided an on-axis, robust ECG signal with a maximally polarized QRS complex. The ECG was connected to a USB-6 DAQ Board via a BNC-2 connector block (National Instruments Corporation, Austin, Tex.). A custom LabView (National Instruments Corporation, Austin, Tex.) program was designed to monitor device pressure, acquire the ECG, and trigger the device. Threshold, R-wave triggering was used. The program provides independent control of device pressurization and evacuation gate times. The device and deployment system were designed for less invasive implantation through a 1 to 2 inches subxiphoid incision in sheep.

Surgical Procedure. The care and use of the sheep in this acute implant study and terminal procedure was conducted at the Texas A&M University College of Veterinary Medicine in accordance with an active animal use protocol approved by the Institutional Animal Care and Use Committee of the Texas A&M University System. The adult sheep, which weighed approximately 70 kg, was premedicated with an anti-anxiety drug (Xylazine 0.075 mg/lb) and an anticholinergic (Glycopyrrolate 0.01 mg/kg). Both drugs were given intramuscularly. After sedation a 16 g catheter was placed in the left jugular vein and anesthesia was induced with Ketamine (4.4 mg/kg) and Diazepam (0.11 mg/g) mixed together and given intravenously (IV) to effect. After induction, the animal was placed sternal and an endotracheal tube of appropriate size was placed and the animal connected to the anesthesia machine. Anesthesia was maintained with isoflurane gas at a concentration of 2-4% throughout the procedure. A lidocaine CRI was started to prevent arrhythmias and Buprenorphine (0.02-0.05 mg/kg) was administered for pain. A two inches lateral incision over the xiphoid process was made, and the xiphoid was removed. A circular hole (1 inch diameter was cut in the pericardium over the heart apex. A one and a half inch thin-walled PVC tube with six guide wires (equally spaced on the outer wall and extending 3 inches beyond the open end) was held oblique to the pericardial hole and the guide wires were inserted into the pericardial sac. Once the position of the tube was verified via flouro, the device was advanced along the guide wires into the pericardial sac (FIG. 4).

Figure 4:
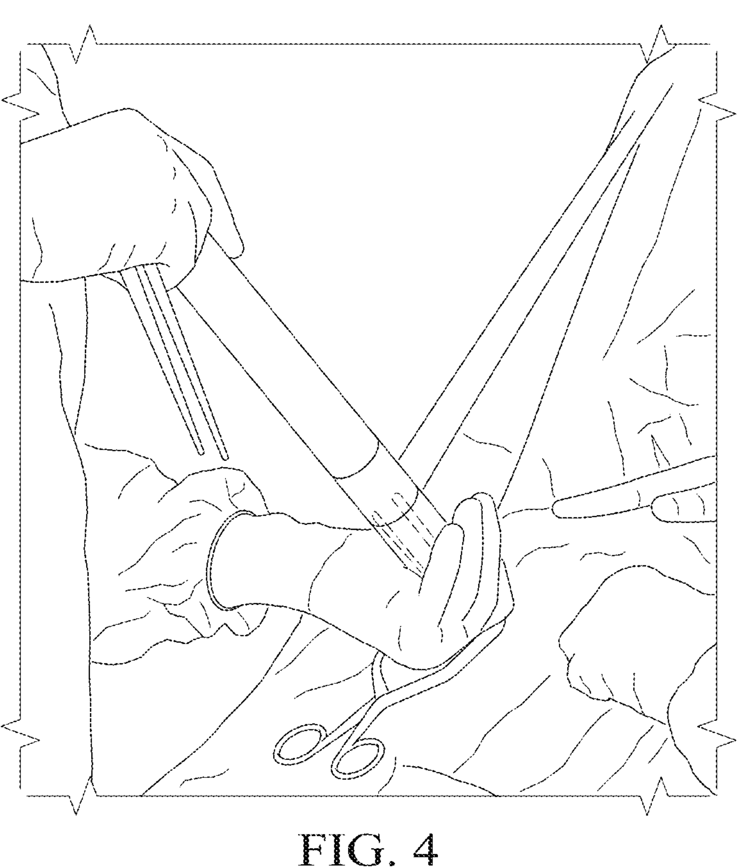
FIG. 4 in an image of the minimally invasive device delivery procedure of one of the embodiments of the instant invention using the deployment tube and pericardial stabilization system with guide wires to ensure proper device placement.

FIG. 4 is an image of the minimally invasive device delivery procedure of the instant invention using the deployment tube and pericardial stabilization system with guide wires to ensure proper device placement.

Hemodynamic Measurements. Using the PVAN software (Millar Instruments Inc., Houston, Tex.), cardiac function was evaluated. Pressure-volume (PV) relationships were determined for three cardiac states: normal, vena cava occlusion, and esmolol induced failure. Measures of heart rate (HR), maximum pressure ($P_{max}$), minimum pressure ($P_{min}$), maximum volume ($V_{max}$), minimum volume ($V_{min}$), end-diastolic pressure ($P_{ed}$), end-diastolic volume ($V_{ed}$), end-systolic pressure ($P_{es}$), end-systolic volume ($V_{es}$), stroke volume (SV), ejection fraction (EF), cardiac output (CO), and stroke work (SW) were obtained. The aforementioned values were calculated for each PV loop acquired. To assess diastolic mechanics, the end-diastolic pressure volume relationship (EDPVR) was measured by use of a balloon catheter inflated in the caudal cava to reduce the preload on the heart. To model acute heart failure, an overdose of esmolol was administered. This included four boluses of 33 mg each for a volumetric subtotal of 13.2 ml (0.5-1.0 mg/kg), and a constant rate of infusion (CRI) of 0.5-2.0 mg/kg/min for a volumetric subtotal of 15.18 ml, and thus a total volume of 28.38 ml esmolol administered.

Delivery and Assessment of Action A1. Changes in the filling pressure of the left ventricle, known as preload, move the end-diastolic point, the lower right-hand corner of the pressure-volume loop. These points can often be approximated in a linear fashion and are collectively known as the end-diastolic pressure-volume relationship (EDPVR), which represents the passive filling mechanics of the left ventricle. Adjustable cardiac support or passive constraint was accomplished by filling the passive chambers of the device with a fixed volume of saline (with X-contrast). Although we applied a fixed volume, this action is termed adjustable cardiac support because the volume of fluid or amount of support can be adjusted post implantation. We tested two separate cases: (1) 0 mL saline, and (2) 40 mL saline. With caval occlusion using a balloon catheter, the filling of the EDV was gradually reduced and the EDPVR for both of the above states was determined and then compared to assess the effectiveness of action A1 to shift the EDPVR upward or leftward (i.e., toward a smaller heart size).

Delivery and Assessment of Action A2. Synchronous active assist was accomplished by oscillating the driving pressure of the device in synchrony with heart contraction. The LabView program detected the ECG trigger and sent a line voltage signal to a custom designed relay system, which opened and closed a circuit of solenoid valves to fill and evacuate the device. A vacuum pump and reservoir system was used to evacuate the device; and a pressure pump and reservoir system was used to activate the device. A pneumatic capacitor network was placed between the device and the pressure source. Activation by use of a pneumatic capacitor isolates the device from the driver and prevents the device from being activated "tectonically" or continuously. Prior DCCD drivers expose the device to a high-pressure source during systole and a vacuum during diastole, whereas the proposed device is only exposed to a charged capacitor during systole and otherwise exposed to vacuum in an "intermittently continuous" manner. When the capacitor is finished discharging, the flow stalls, the vacuum port is opened, and the device relaxes. To prevent the device from being exposed to a continuous high-pressure source, the port to the device is closed when the capacitor is charged, and the port to the pressure source is closed when the capacitor is discharged toward the device. Using such a drive mechanism, device activation is restricted to intermittent pressurization. The capacitor network allows for variable capacitance. The pressure in the reservoir was tuned with the capacitor network to achieve the desired transport profile. To assess the ability of the device to provide synchronous cardiac assist for a failing heart, we applied 0 and 20 mmHg of systolic assist for two cardiac states: (1) normal or baseline contractility, and (2) low contractility or esmolol induced, acute heart failure. For the normal cardiac state an active assist of 20 mmHg was applied for approximately 5-10 cardiac cycles, after which the active assist was shut off for approximately 5-10 cardiac cycles. The same procedure was used for the esmolol induced failure state, first with an active assist of 20 mmHg. Pressure-volume loop analysis was used to assess cardiac function during the varying amounts of assist.

Design and Assessment of Feature F1. Implantation is designed to be accomplished using guide wires attached to a deployment tube containing the device. Fixed suture loops are sewn to the base of the device. The guide wires are then passed through the suture loops and the device is preloaded into the deployment tube. Once the guide wires are properly placed inside the pericardial space, the device can be pushed out of the deployment tube following the guide wires flaring around the heart into the correct position. In order to get the guide wires placed properly, the tip of each wire is sutured together to form a scoop or spoon shape. The scoop is inserted into the pericardial opening at which time the suture holding the nitinol and guide wires together is released allowing them to recoil into the correct position. Fluoroscopic imaging was used to assess proper device placement.

Design and Assessment of Feature F2. The device was made of thin nylon film bladders and nitinol wires that formed an open frame so that it was collapsible when depressurized. The design constraint of collapsibility when depressurized was sought so that the device itself did not impede cardiac function. To assess this feature, pressure-volume loop analysis was done prior to implantation (prior to opening the chest) and after implantation (after chest closed). Cardiac function preimplant and post implant were subsequently compared.

Design and Assessment of Feature F3. The outer half of the device chambers formed a continuous, inextensible outer shell of nylon whereas the inner half was in direct contact with the heart surface rather than fully distended. Consequently, the device was designed to apply uniform pressure to the entire epicardial heart surface, as uniform pressure was likely to preserve cardiac curvature i.e., it was unlikely to invert the ventricular wall or cause similar aberrant motions. To assess the heart shape during device activation, the heart silhouette was observed in fluoroscopy videos taken during maximal device activation. The air chambers were easily identified with X-imaging (light areas). The contrast filled passive chambers are also evident (dark areas), as well as the myocardium (gray).

Design and Assessment of Feature F4. The chambers of the device were tapered with minimal space near the apex and maximal space near the base. Consequently, when the device was activated it took on a cuplike shape as opposed to a ball-like shape-the latter being the expected shape for an inflated object that does not have chamber partitions. The advantage of a cuplike activated shape is that the heart is likely to be retained in the device rather than expelled from the device. This is so because there is no free air in the chest to fill the space between an expelled heart and the cup cavity. Rather, it is expected that the device will be pneumatically coupled and coaxially fixed to the heart without the need for suturing. To assess this feature, the motion of the heart silhouette relative to the wire frame on the device was observed in fluoroscopy videos.

Results: Cardiac Decompression via Active Assist. The application of 20 mmHg of pressure to the epicardial surface of the heart during systole results in an immediate increase in stroke volume with concomitant decrease in both end-diastolic and end-systolic volumes, to new "assisted" equilibrium states.

Figure 5:
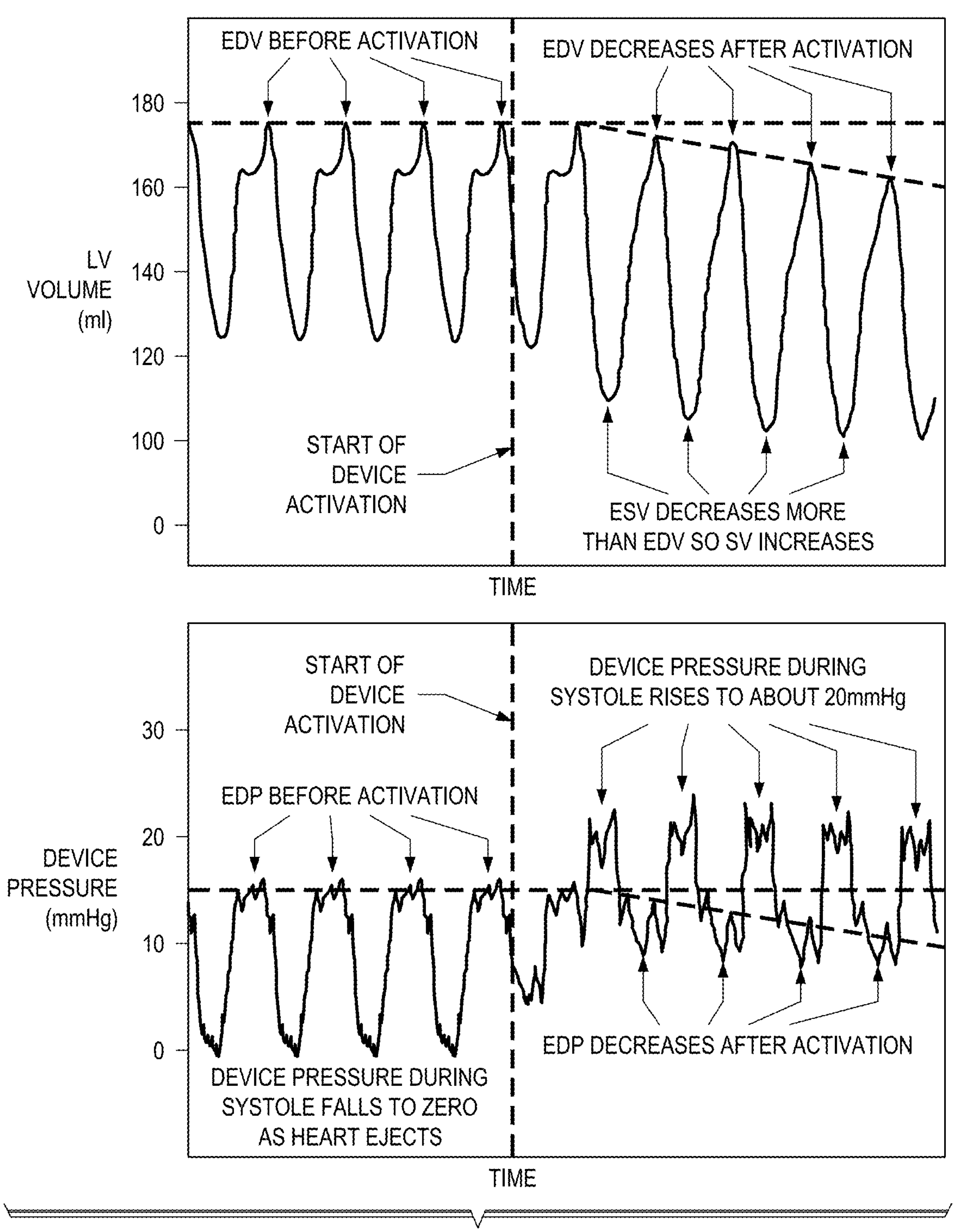
FIG. 5 is a graph of the LV volume during transition from no assist to 20 mm Hg of assist. The top portion illustrates the end-diastolic volume (EDV) while the bottom illustrates the device pressure during transition from no assist to 20 mm Hg of active assist.

FIG. 5 is a graph of the LV volume and device pressure during transition from no assist to 20 mm Hg of assist. The top portion illustrates the end-diastolic volume (EDV) while the bottom of FIG. 5 illustrates the device pressure during transition from no assist to 20 mm Hg of active assist. The upper tracing in FIG. 5 is the volume channel from the pressure-volume catheter; again, the lower tracing illustrates device pressure. As seen in the top portion of FIG. 5, the application of 20 mm Hg of pressure to the epicardial surface of the heart during systole results in an immediate increase in stroke volume with concomitant decrease in both end-diastolic and end-systolic volumes, to new "assisted" equilibrium states. Note that though the end-diastolic volume (EDV) decreased with assist, the reduction in end-systolic volume (ESV) was greater; thus the stroke volume is actually increased. FIG. 5 (Bottom) is an image of the device pressure during transition from no assist to 20 mm Hg of active assist. Note that the device pressure goes from 0 mm Hg during systole (before device activation) to 20 mm Hg during systole (following device activation). The end-diastolic pressure (EDP) in the device is constant at 15 mm Hg before assist begins and falls to 10 mm Hg after assist starts. The EDP is high in this case because of passive constraint (e.g., action Al below); and the result is that the active assist decompresses the LV and subsequently decreases EDP back into the normal range. This phenomenon is referred to as cardiac decompression with cardiac assist.

Figure 6:
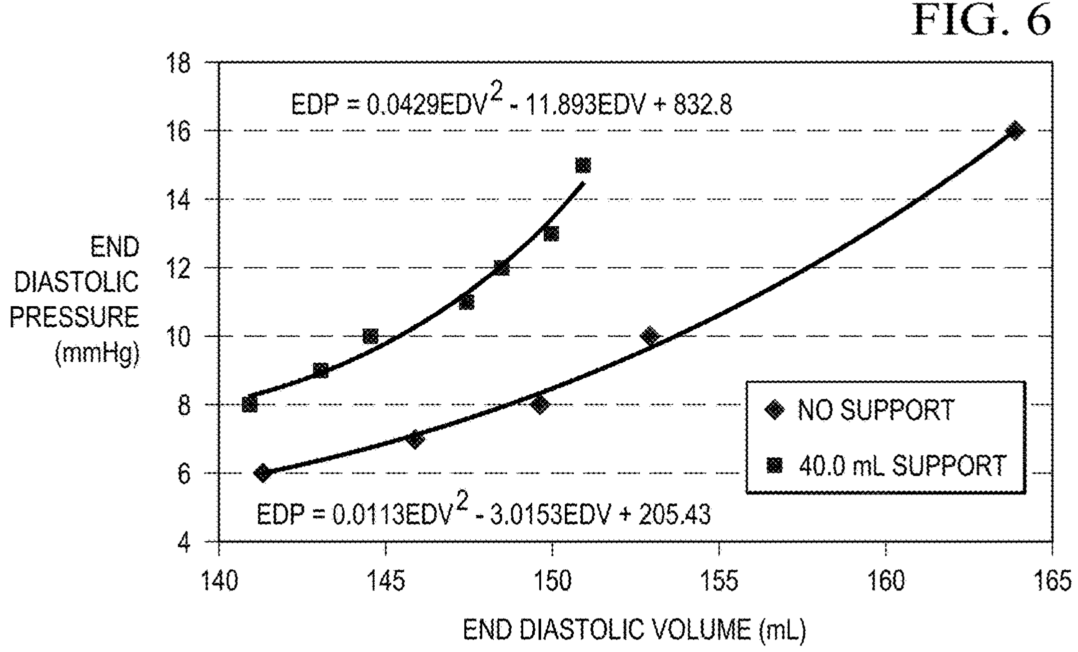
FIG. 6 is a graph of the shift of end diastolic pressure-volume relationship (EDPVR) with adjustable cardiac support.

Action A1: Adjustable Cardiac Support or Passive Constraint to Reduce Heart Size. FIG. 6 is a graph of the shift of EDPVR with adjustable cardiac support. Two cases were investigated, (1) no passive support, i.e., no saline in the passive component and (2) passive support with 40 ml saline in the passive component of the device. As the preload is gradually reduced by slowly occluding the vena cava, the pressure-volume relationship is altered. The end-diastolic data points for each case are plotted. The resulting curve is the EDPVR. Note that support shifts the EDPVR to the left, which could be beneficial as disease tends to shift the EDPVR to the right. With use of caudal cava occlusion, the EDV was decreased and the end-diastolic points for multiple PV loops are plotted in FIG. 6 together they represent the EDPVR. The plots of the EDPVR for no support versus the 40 mL support cases show that the EDPVR shifted leftward. This shift in the EDPVR indicates a decrease in the size of the left ventricle relative to filling pressure, i.e., the ventricle maintains the same filling pressure at a smaller volume.

The passive component can include an inlet/outlet to allow the volume of the passive component to be adjusted as necessary given the size and shape of the heart as it is remodeled or the pressure needed to be exerted on the heart in the passive state. This inlet/out allows fluid to be added to the device to increase the volume of the passive component. This mechanism of altering the volume of the passive component may be accomplished prior to implantation, after implantation or both. In addition, the device of the present invention may include 1, 2, 3, 4, 5, 6, 7, 8, 9, 10, 11, 12, 13, 14, 15, 16, 17, 18, 19, 20 or more separate chambers that may be positioned around the device in a single column design or in a single column design having a subdivision of 2, 3, 4, 5 or more rows of chambers in each column. The final configuration will depend on the size, shape, damage and other factors but the passive chambers can be configured to accommodate any heart by adjusting the volume of the individual chambers, the number of individual chambers and the layout of the individual chambers. In addition, the individual chambers may have individual inlet/outlets to accommodate different pressures (and support) at different locations about the heart.

The passive component can include individual chambers in any number desired and include a sensor to monitor the passive fluid pressure waveform for assessing performance of the device. This passive fluid pressure waveform can be monitored internally and relayed to an external recorder and/or display. In addition to the pressure of the passive chamber, the sensor can monitor end inflation pressure level, deviations in pressure to diagnose a leak or weakening of the device. The sensor may also be used to measure the pressure in the active device and the active bladders. In addition, a separate channel or sensor may be used for infusing/monitoring fluid in the passive chambers along the length of the main pneumatic pumping line and a pressure sensor for monitoring that line as part of the driver.

In addition, the shape of the passive bladders may be designed to adapt to the shape of the heart. For example, the inner passive bladder may have a "heart shaped" profile to better contour to the heart. However a convex or concave profile may be used in specific instances. Similarly, a combination of these profiles may be used to accomplish specific support or remodeling, e.g., heart shaped at the upper portion of the bladder and convex (or concave) at the bottom nearest the apex; convex (or concave) at the upper portion of the bladder and heart shaped at the bottom nearest the apex; heart shaped bladders on the left portion of the device and convex (or concave) shaped bladders on the right portion of the device; heart shaped bladders on the right portion of the device and convex (or concave) shaped bladders on the left portion of the device; alternating heart shaped bladders and convex (or concave) shaped bladders; etc.

Figure 7:
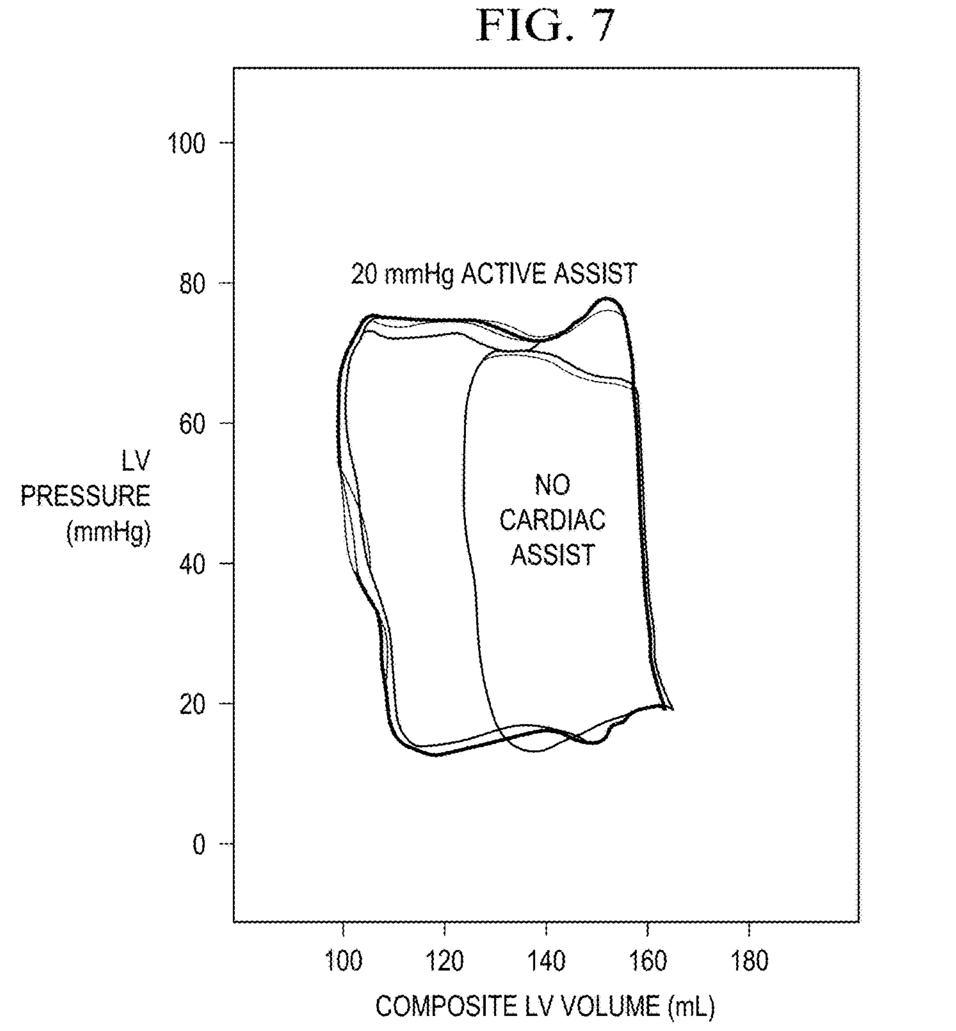
FIG. 7 is an image of pressure-volume loops of the left ventricle for the esmolol induced failure state with 0 mm Hg active assist transitioned to 20 mm Hg active assist.

Action A2: Synchronous Active Assist to Correct and Increase Heart Motion or Stroke Volume, Stroke Work, Ejection Fraction, and/or Cardiac Output. For the esmolol induced failure state, an active assist of 20 mm Hg was applied for approximately 5 to 10 cardiac cycles, after which the active assist was shut off for approximately 5 to 10 cardiac cycles. A comparison of the pressure volume loops for both cases is shown in FIG. 7. FIG. 7 is an image of pressure-volume loops of the left ventricle for the esmolol induced failure state with 0 mm Hg active assist transitioned to 20 mm Hg active assist. The improved stroke work is evident in the increase in area.

Figure 8:
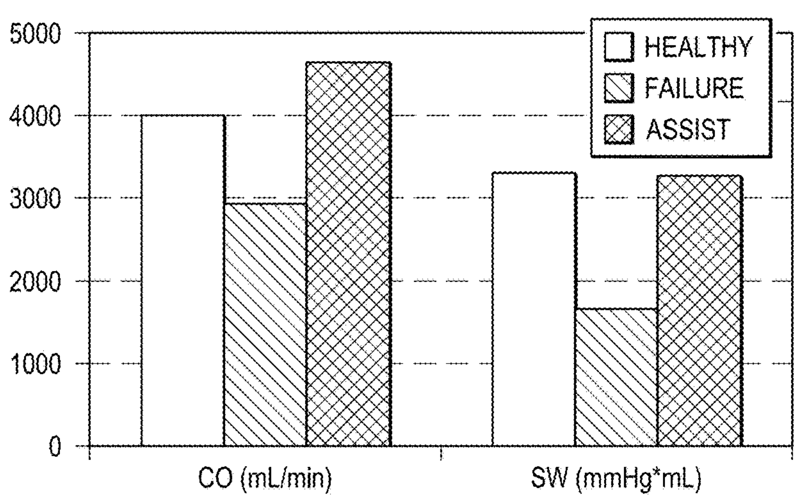
FIG. 8 is a graph comparison of the recovery of stroke work and cardiac output in healthy, Esmolol failure, and assisted failure cases.

FIG. 8 is a graph comparing the recovery of stroke work and cardiac output in healthy, Esmolol failure, and assisted failure cases. Notice the significant improvement in CO and doubling of SW for the esmolol induced failure state when active assist of 20 mm Hg is applied. As illustrated, CO and SW can be returned to healthy levels with assist. FIG. 8 illustrates the changes in two critical measurements of cardiac performance for the healthy cardiac state, esmolol induced heart failure state, and assisted failure state. For the esmolol induced heart failure state, high doses of esmolol infusion reduced CO by 29.3% and SW by 49.9%. When active assist of 20 mm Hg was applied to the esmolol induced heart failure state CO and SW increased by 58.8%, and 99.5%, respectively.

Figure 9A:
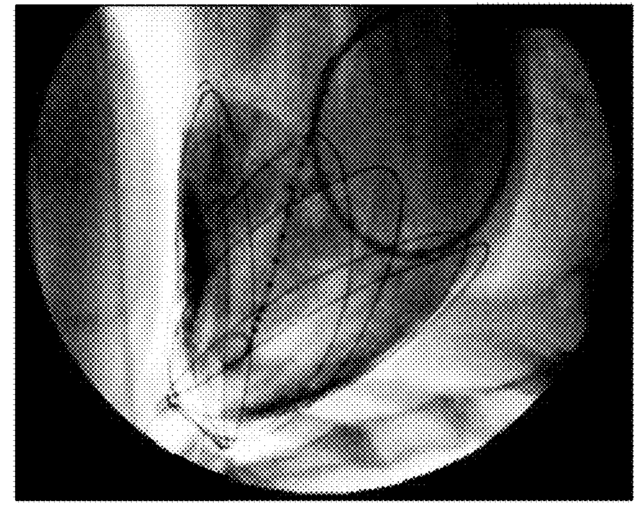
Figure 9B:
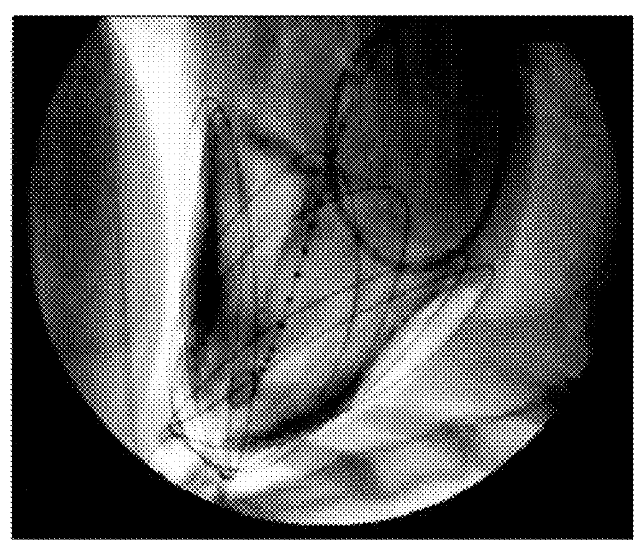
FIG. 9B is an image of the air filled active component contacting the heart during end-systolic configuration.

FIG. 9A is an image of the inner passive component of the device conforming to the heart during end-diastolic configuration, whereas FIG. 9B is an image of the air filled active component contacting the heart during end-systolic configuration. Simultaneous application of actions A1 and A2 are shown in the figure at two different points in the cardiac cycle. Fluoroscopic imaging was used to assess the simultaneous application of actions A1 and A2. Radio-opaque die was injected into the passive chambers. The working fluid in the active chambers is air, which is easily discernible via fluoroscopy. In FIG. 9, the dark regions near the heart wall correspond with the contrast filled inner passive component of the device. When activated, air fills the outer active component, which compresses the inner passive component of the device. Fluid in the passive component is displaced and pressure is applied uniformly to the heart. In FIG. 9, note the presence of both support fluid (radiodense) and assist fluid (radiolucent).

Figure 10:
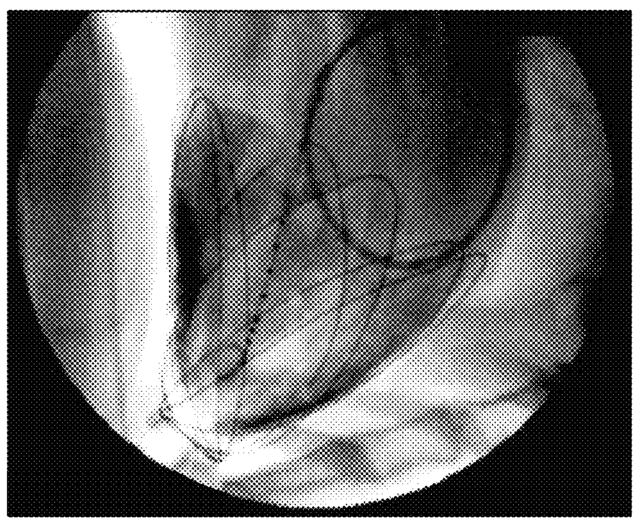
FIG. 10 is an image of the device with saline filled inner passive chambers conforming to the heart.
Figure 11A:
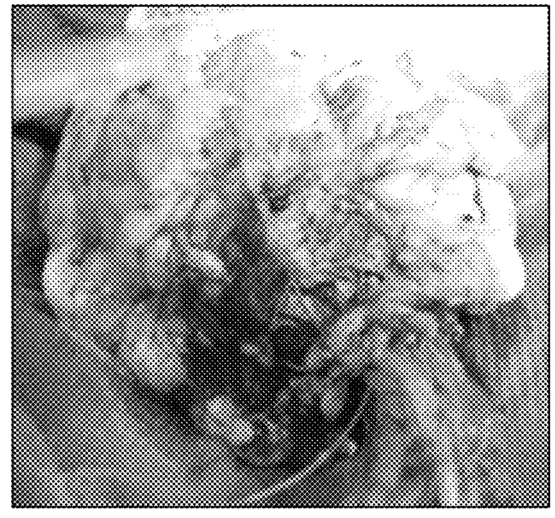
FIGS. 11A-11B are images of the gross pathological examination of device within pericardial sac closed (FIG. 11A) and open (FIG. 11B) to reveal the device around the heart.
Figure 11B:

Feature F1: Delivery and Deployment via Minimally Invasive Surgical Procedures. Contrast was injected into the passive chambers for visual confirmation of placement and action. The sternum was not opened, nor were intercostal spaces opened during device deployment through a small subxiphoid incision. FIG. 10 is an image, using fluoroscopy, of the fully deployed device with saline filled inner passive chambers conforming to the heart. Postmortem analysis of the heart and pericardial sac resected together shows the devices was properly deployed into the pericardial sac. FIGS. 11A-11B is an image of the gross pathological examination of device within pericardial sac closed (FIG. 11A) and open (FIG. 11B) to reveal the device around the heart.

Figure 12:
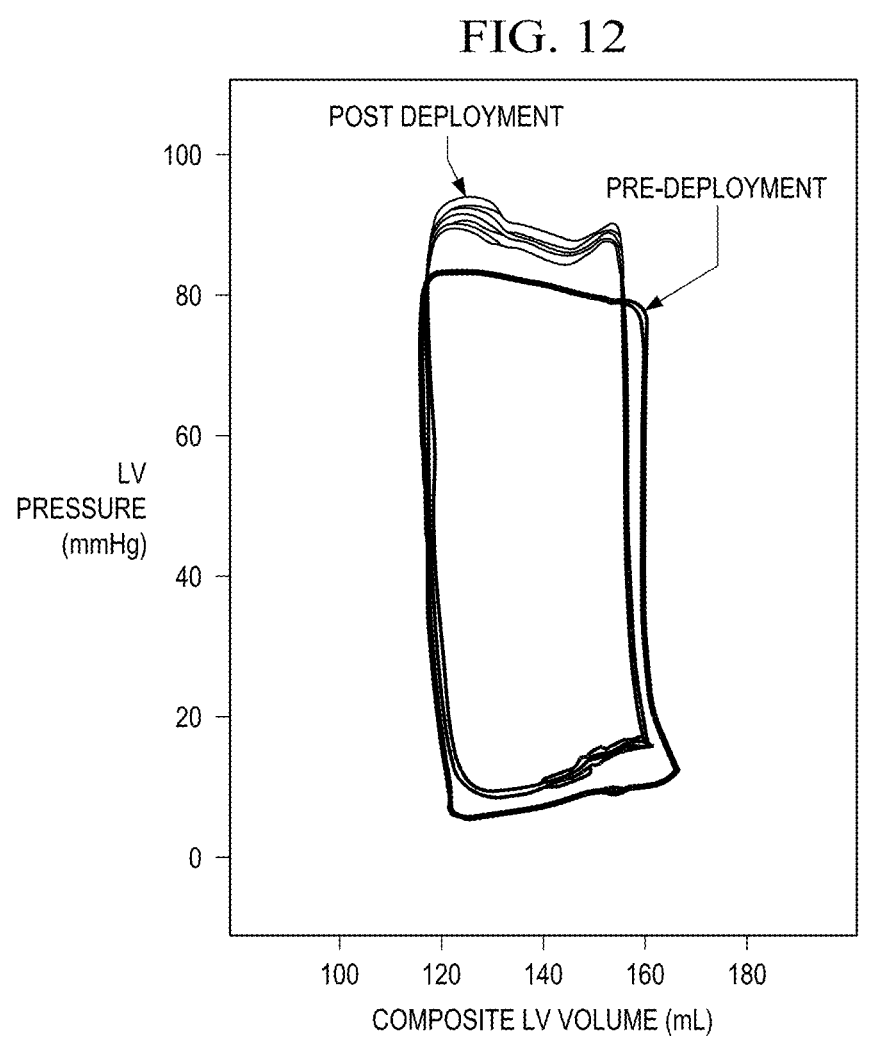

Feature F2: Device Does Not Impede Heart Function When Inactive. FIG. 12 is an image of the pressure-volume loops of the left ventricle prior to device deployment and after deployment. Stroke work and cardiac output were not significantly affected. Stroke volume (SV), ejection fraction (EF), cardiac output (CO), and stroke work (SW) were not significantly affected by device placement. The heart rate increased by approximately 10% after device implantation; however, remained well within the normal range.

Feature F3: Device Does Not Invert Heart Curvature When Activated. Inspection of images obtained via fluoroscopy revealed no evidence that the device inverts the curvature of the heart when activated. Images were acquired continuously at a rate of 15 frames per second over several cardiac cycles.

Figure 13A:
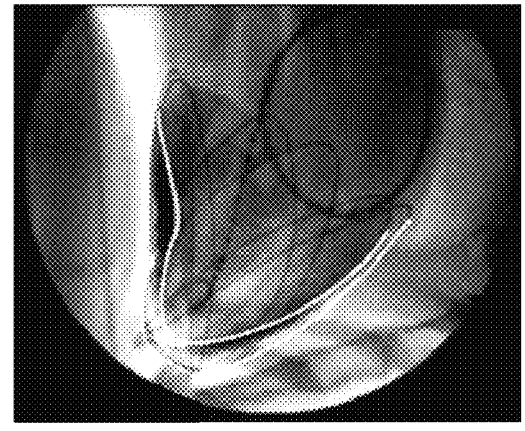
FIG. 13A is a fluoroscopic image of the device conforming to the heart during end-diastolic configuration.
Figure 13B:
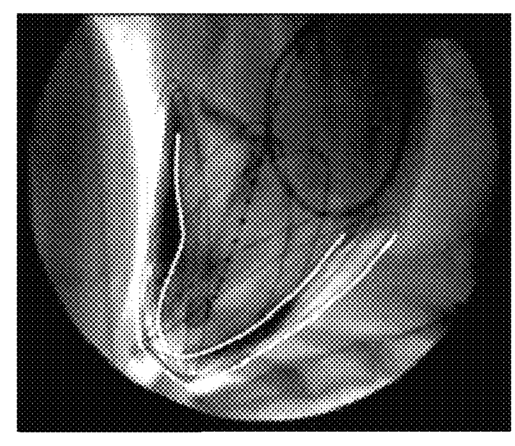
FIG. 13B is a fluoroscopic image of the device conforming to the heart during end-systolic configuration.
Figure 13C:
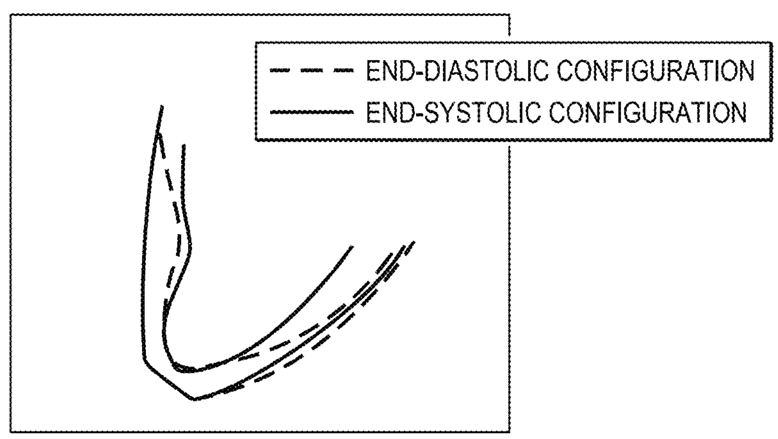
FIG. 13C is an overlay of the heart during the end-diastolic configuration and the end-systolic configuration.

FIG. 13A is a fluoroscopic image of the device conforming to the heart during end-diastolic configuration, FIG. 13B is a fluoroscopic image of the device conforming to the heart during end- systolic configuration, FIG. 13C is an overlay of the heart during the end-diastolic configuration and the end-systolic configuration. During systole the device is maximally loaded with air that is easily discernible in the images. Although the size is reduced from ED to ES, the heart shape remained similar in the images. The edge detection and resulting contour plots were accomplished manually. Qualitative assessment in this manner revealed no evidence of curvature inversion or gross changes in cardiac shape during systolic activation. Evidence that fluid in the passive chambers is displaced during activation is distinguishable from the images.

Figure 14A:
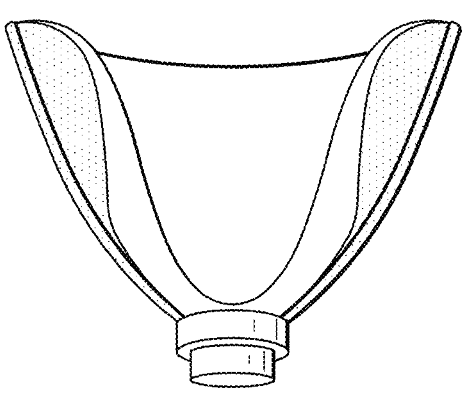
FIG. 14A is an image of the chambers of the device designed such that that cavity takes on a cuplike shape when activated and FIG. 14B is a simple contour drawing of the Anstadt cup.
Figure 14B:
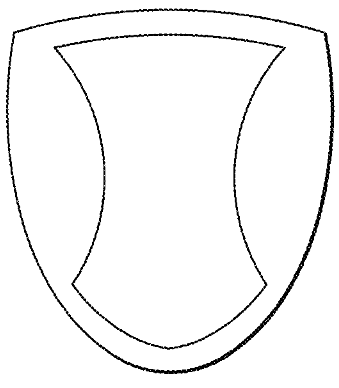

Feature F4: The device of the present invention does not dislodge, extrude or expel the heart when activated. FIG. 14A is an image of the chambers of the device designed such that the cavity takes on a cuplike shape when activated and FIG. 14B is a simple contour drawing of the Anstadt cup. The device of the present invention prevents device-induced curvature inversion and also allows the heart to be held in place in the device via an intrinsic pneumatically attachment. FIG. 14B illustrates a simple contour drawing of the Anstadt cup (see Anstadt et al. 2009), which like all conventional direct cardiac compression devices are designed to invert the curvature of the heart. Inversion of wall coverage is likely to lead to increased ejection fraction and such wall motion is abnormal or aberrant. The present device takes on a rigid cup like shape (i.e., structurally supported cavity) when it is pressurized, and this naturally draws the heart into the device such that suturing to the heart is not required.

After air in the mediastinum is removed, the heart and device are pneumatically locked in a coaxial configuration. This is seen by fluoroscopy of device assist when actively pressurized during systole. The air filled bladders are easily visible on fluoro, and it is evident that the heart is not displaced by device activation; rather, the heart diameter decreases when bladders inflate.

The present invention provides the capability to provide simultaneous adjustable passive support and active assist via direct cardiac compression with a single non-blood contacting device that is nonobligatory, delivered via minimally invasive surgical procedures, remains in place via an intrinsic pneumatic attachment, and designed to apply uniform compression (i.e., compression without inverting the curvature of the heart). To our knowledge, there are no devices capable of simultaneously providing adjustable passive support and active assist. The assist component of the present device is non-blood contacting and thus does not bear some of the risks associated with many current devices, i.e., blood pumps. The magnitude of assist can be graded and is synchronized with the heart function. Unlike existing blood pumps yet similar to aortic balloon pumps, the present device can be turned off without impeding heart function; thus making it nonobligatory. The versatile combination of support and assist provides the cardiologist with powerful therapeutic options to treat a wide variety of patient-specific anomalies—with the ultimate target being rehabilitation of the heart and recovery of cardiac function and performance. In the present paradigm there are non-blood contacting devices designed to inhibit enlargement, i.e., cardiac support devices (CSD) such as the Acorn CorCap, and non-blood contacting devices designed to restore circulation, i.e., direct cardiac compression devices (DCCD) such as the Anstadt Cup. Incorporating a passive support component that is adjustable post implant and an active assist component that is nonobligatory and designed to improve ejection fraction without inducing aberrant inversions of curvature, the present device is potentially capable of achieving the therapeutic objectives of both CSD and DCCD technologies and represents substantial advancements for both methods of intervention with the potential for cooperative benefits i.e., combinatorial benefits that exceed the sum of benefits from each action alone.

The biomechanical model of heart failure proposed by Mann and Bristow was developed with the understanding that neurohormonal compensatory mechanisms that are triggered following some adverse cardiac event essentially disguise symptoms of underlying disease and actually contribute to the progression of maladaptive cardiac remodeling, which is characterized by a geometrical change in the architecture of the left ventricle and aberrant cardiac motion. The effectiveness of therapeutic strategies incorporating ACE inhibitors and b-blockers to alleviate the adverse effects of neurohormonal compensation seem to support the concept of a "neurohormonal model of heart failure," wherein over expression of biologically active molecules is implicated as driving disease progression. Unfortunately, though initially very effective, these strategies lose effectiveness with time and thus, the neurohormonal model fails to explain the relentless progression of disease. The biomechanical model predicts "when the deleterious changes in cardiac function and cardiac remodeling are sufficiently advanced, they become self-sustaining and hence are capable of driving disease progression independently of the neurohormonal status of the patient." This suggests that aberrant mechanical cues emanating from the diseased mechanical environment are translated appropriately by otherwise healthy cells and thus, healthy cells inadvertently drive processes that contribute to the progression of heart failure. With this understanding, pathologic cardiac mechanics is identified as an important but generally neglected target for therapy, particularly in the interest of cardiac recovery and rehabilitation.

Conventional cardiac support devices (CSD) are designed to constrain the dilatation associated with end-stage failure. With the exception of the device described in Ghanta et al., these devices (e.g., CorCap and HeartNet) are not adjustable and, moreover, resist adjustment because of extensive fibrosis around the heart. While these devices have demonstrated an ability to limit enlargement, the associated fibrous adhesions inhibit cardiac motion and greatly complicate any further intervention. In contrast, the fluid filled passive chambers of the present device, isolate the heart from surrounding tissue and fibrous adhesions, and thus impart minimal impact on cardiac motion. Whereas, conventional CSD essentially represent a "one-shot" approach to treatment, the device described herein may be repeatedly adjusted post implant by injection/evacuation of fluid into a subcutaneous port. Though the CSD device is adjustable in vivo, it requires tethering via continuous suture along the AV groove. The present device does not require such fixation as it is held in place by an intrinsic pneumatic attachment. It is hypothesized that with use of an adjustable cardiac support device, to incrementally constrain the heart to smaller configurations over a period of several months (with 1-2% reduction every week), it may be possible to return heart size to normal-regardless of the etiology. Reduction of heart size is highly significant because size and function are inversely related in failing hearts. Furthermore, a reduction in size is likely to reduce the risk of arrhythmias, the primary cause of death for patients with end-stage heart failure. The ability to provide simultaneous assist is likely essential to safely achieve progressive constraint as (1) assist effectively decompresses the passively constrained heart to reduce pulmonary congestion; and (2) assist may be required in the event of cardiogenic shock.

The present invention described herein has potential to serve as (1) a means of investigating the effects of the mechanical environment on cardiac physiology; and (2) a therapeutic device for the treatment of congestive heart failure. To our knowledge it is the first device capable of providing adjustable passive support and synchronous active assist simultaneously. Moreover, it is non-blood contacting, nonobligatory, and can be delivered via minimally invasive surgical procedures. The versatility of the device provides for a wide range of proactive intervention possibilities. As a therapeutic device, it represents advancements to existing CSD and DCCD technologies, and more importantly, is the first device designed to provide rehabilitative therapy for the heart. The present invention provides conditions under which natural growth and remodeling processes are guided in a therapeutic manner. The present device provides versatility in manipulating the mechanical environment such that the efficacy of a device-based intervention capable of targeting recovery and/or rehabilitation via manipulation of the mechanical environment can be tested.

The present invention provides an implantable direct cardiac compression device with a collapsible structure that assumes the shape of the left ventricle keeping an inwardly directed pressure to prevent the enlargement of the ventricle and provides adjustment of the end diastolic volume for limiting/reducing the end systolic volume.

The present invention provides a contoured heart assist device that reduces dyskinesis and hypokinesis. The device includes a selectively inflatable end-systolic heart shaped bladder with one or more contoured supports configured to surround at least a portion of the heart to provide curvatures similar to the proper shape of the heart when pressurized and one or more fluid connections in communication with the selectively inflatable end-systolic heart shaped bladder for pressurization and depressurization.

The one or more contoured supports form one or more inflatable compartments having an expanded curvature optimized to fit generally the proper end-systolic shape of the heart. The selectively inflatable end-systolic heart shaped bladder includes an inner membrane that is at least partially folded when depressurized and at least partially unfolded when pressurized. In another embodiment, the selectively inflatable end-systolic heart shaped bladder includes an inner membrane that is at least partially folded when depressurized and at least partially unfolded when pressurized and an outer membrane that is at least partially folded when depressurized and at least partially unfolded when pressurized. Other embodiments may include various combinations thereof.

The selectively inflatable end-systolic heart shaped bladder is generally collapsible when depressurized and is reinforced to resist radially outward expansion during pressurization. The device of the present invention may take many configurations depending on the particular treatment. For example, the selectively inflatable end-systolic heart shaped bladder may include 12 inflatable tapered compartments formed by the one or more contoured supports to provide an expanded curvature similar to the proper end-systolic shape of the heart; however, other embodiments may have 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more inflatable tapered compartments. Furthermore, the distribution of the inflatable tapered compartments may vary from the design of 4 chambers on the RV side and 8 chambers that are mostly on the LV but also overlapping the interventricular sulci. For example, the device may have 1, 2, 3, 4, 5, 6, 7, 8, 9, 10, 11, 12 or more chambers on the RV side and 1, 2, 3, 4, 5, 6, 7, 8, 9, 10, 11, 12, 13, 14, 15, 16, 17, 18, 19, 20, 21, 22, 23, 24 or more chambers that are mostly on the LV and overlapping the interventricular sulci. The chambers' distribution determination for a particular application and treatment is within the scope of the skilled artisan.

The inflatable tapered compartments are connected to a pneumatic pressure source through an inlet port and an outlet port. The device is inflated with a positive pressure during systole and deflated via suction during diastole. Although, other configurations and multiple connections are also possible depending on the particular application and configuration. The inlet port and an outlet port may be connected through a single connection for applying the positive pressure and the suction or negative pressure; alternatively, multiple connections may be used. In addition, the inlet port and an outlet port may be made anywhere about the boundary of the selectively inflatable end-systolic heart shaped bladder, e.g., near the base or near the apex.

Many devices of the present invention may be inserted through a small incision. Many devices may also be attached to the atrial appendages via clamps that may also be used to synchronize the device to the electrocardiogram (ECG) or to pace the heart relative to the device activation.

The device may be implanted with minimal attachment or sewing to the heart. Clamps on the atrial appendages are sufficient and useful for sensing the ECG or for pacing the heart. The access port on the apex (i.e., the hole in the bottom of the device) is useful for implantation and for removing fluid that could accumulate between the heart and device. Additionally, a biocompatible lubricant, anti-clotting, anti-fibrosis, or antibiotic agent may be injected into the space between the heart and device. So that the device may be removed easily after weaning, the device may be covered with a film that retards fibrous adhesions, and fluid might be pumped through the access port on the apex to separate the heart from the device.

The present invention provides a method for implanting a heart assist device in a minimally invasive manner, for example, a small sub-xiphoid incision. Also, it enables a failsafe mechanism. In particular, the device does not hinder cardiac performance when the device is deflated or deactivated. In the embodiments herein, we completely deflate the device (default to vacuum) to make it soft and collapsible.

The purpose of the interior supports is to make the pressurized shape like the end-systolic shape of the heart. In similar fashion, the interior supports of an air mattress make the pressurized shape that of a mattress as opposed to that of spheroid. This prototype is made of latex, yet a device for implantation would be made of a flexible biocompatible polymer such as polyurethane or of a flexible biocompatible composite material. Being made of a highly flexible material, it is collapsible. The apical hole in the device is a useful feature that aids with implantation, e.g., by being able to draw the heart apex into the device via a suction cup threaded through the apical hole in the device. The apical hole is also useful for removing any fluid or air that leaks out of the device that would accumulate between the heart and device. In addition, the apical hole may be used to access the heart as necessary. For example, the apical hole may be used to flow a fluid such as compressed air into the device to separate the heart from the device to allow removal of the device.

The direct compression cardiac device also includes one or more resilient members positioned about the resilient inner panel. The resilient members may be used to supply resistance to the heart either with or without the addition of bladders. The number, size, length, diameter, cross-section, profile, width, composition and other physical characteristics may be changes as necessary to produce the desired resistance. The one or more resilient members may be individually a metal, an alloy, a memory metal, a composite, a polymer, a plastic or a combination thereof. One specific embodiment of the present invention includes memory metals or metal alloys, e.g., zinc, aluminum, copper, aluminum, nickel, and titanium; copper-zinc-aluminum, copper-aluminum-nickel, and nickel-titanium (NiTi) alloys and combinations thereof. Other examples include: Ag-Cd at differing percentages of Cd (e.g., 44-49%); Au-Cd at differing percentages of Cd (e.g., 46.5-50%); Cu-Al-Ni at differing percentages of Al (e.g., 14-14.5 wt. %) and at differing percentages of Ni (e.g., 3-4.5 wt. %); Cu-Sn at differing percentages of Sn (e.g., 15%); Cu-Zn at differing percentages of Zn (e.g., 38.5-41.5 wt. %); Cu-Zn-X (X=Si,Sn,Al) at differing percentages of X (e.g., 0-10 wt. %); In-Ti at differing percentages of Ti (e.g., 18-23%); Ni-Al at differing percentages of Al (e.g., 36-38%); Ni-Ti at differing percentages of Ni (e.g., 49-51%); Fe-Pt at differing percentages of Pt (e.g., 25%); Mn-Cu at differing percentages of Cu (e.g., 5-35%); Fe-Mn-Si; Pt alloys; Co-Ni-Al and Co-Ni-Ga. Furthermore, the position and the method of attaching the resilient members about the resilient inner panel may be altered as necessary to provide resistance.

The present invention may also include one or more sensors, one or more electrodes, one or more conductive elements, one or more monitoring devices, one or more transmitters, one or more receivers, one or more actuators, or a combination thereof in contact with the direct compression cardiac device. One or more bioactive agents selected from antimicrobials, antibiotics, antimitotics, antiproliferatives, antisecretory agents, non-steroidal anti-inflammatory drugs, immunosuppressive agents, antipolymerases, antiviral agents, antibody targeted therapy agents, prodrugs, free radical scavengers, antioxidants, biologic agents or combinations thereof may be implanted, coated or disseminated The present invention may be used to create the proper end-systolic shape of the heart, end-diastolic shape of the heart or both. The contoured supports can be used to provide an expanded curvature similar to the proper end-systolic shape of the heart and/or the proper end-diastolic shape of the heart. A direct cardiac compression device applies force to the exterior, epicardial boundary of the heart to restrict inflow and modulate right flow versus left flow through the heart to promote contraction strain patterns on a diseased or damaged heart to reduce dyskinetic or hypokinetic motions.

Generally, when a material is implanted in the body, the body recognizes the presence of the foreign material and triggers an immune defense system to eject and destroy the foreign material. This results in edema, inflammation of the surrounding tissue and biodegradation of the implanted material. As a result the biomedical implantable material must be carefully selected. Examples of suitable, biocompatible, biostable, implantable materials include but are not limited to polyetherurethane, polycarbonateurethane, silicone, polysiloxaneurethane, hydrogenated polystyrene-butadiene copolymer, ethylene-propylene and dicyclopentadiene terpolymer, and/or hydrogenated poly(styrene-butadiene) copolymer, poly(tetramethylene-ether glycol) urethanes, poly(hexamethylenecarbonate-ethylenecarbonate glycol) urethanes and combinations thereof. In addition, the present invention may be reinforced with filaments made of a biocompatible, biostable, implantable polyamide, polyimide, polyester, polypropylene, polyurethane, etc., or may be made of biocompatible, biostable, implantable composite materials.

The present invention includes a mechanism of insertion embedded in the device, consisting of two wire frames, in which one frame twists relative to the other causing the device to decrease in size in the radial direction, so that it may be inserted into a deployment tube. Upon exiting the deployment tube, further twist of the wire frames relative to one another may cause a flowering effect or flaring effect at the base of the device to begin expansion of the device around the apex of the heart. Fully untwisting the device allows the device to take on the cup-like shape of the heart. The present invention includes a method of using the previously discussed mechanism for making minor adjustments to the size of the device. Twisting the outer frame relative to the inner frame results in a smaller device in the deflated state and untwisting the device results in a larger device in the deflated state (Twist for sizing).

The present invention includes a mechanism of insertion in which the delivery system consists of a retractable framework such as wire loops that slide into pockets on the exterior or interior of the direct cardiac compression device. In addition to a pocket structure, the device may be a mechanism that functions as an attachment mechanism. For example, the attachment mechanism may be a slot or groove, a peg and notch, a magnetic connection, or other mechanisms known to the skilled artisan to serve a similar function. As the wire loops are pushed from the delivery system they fan outward into the pockets of the DCCD, creating the flowering or flaring effect necessary for the expansion of the device around the apex of the heart. Once the DCCD is in the correct position the wire loops can be retracted and the delivery system can be removed from the pericardial opening. Prior to deployment, the delivery system engages the pockets of the DCCD and both the delivery system and device can be placed inside an insertion tube. In the pre-deployment state, either the DCCD can rest inside the delivery system or the DCCD can rest outside the delivery system.

Figure 15A:
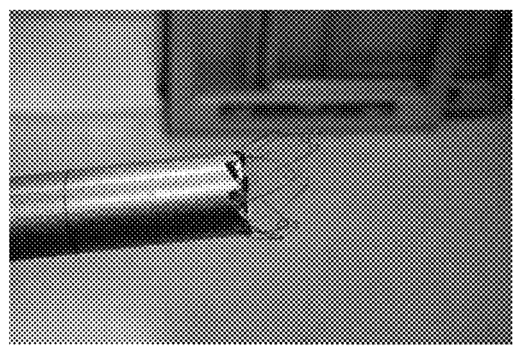
FIGS. 15A-15C are images of the deployment stages of one insertion mechanism used in deploying a DCCD.
Figure 15B:
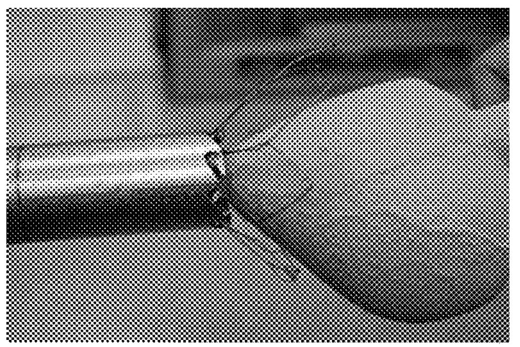
Figure 15C:
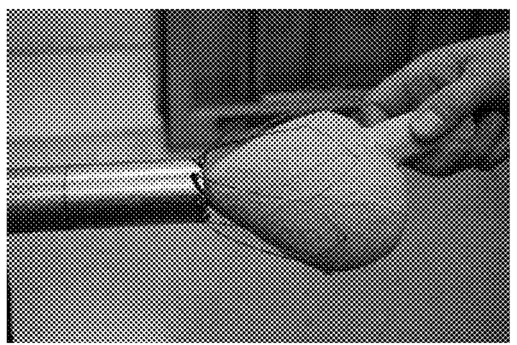
Figure 16A:
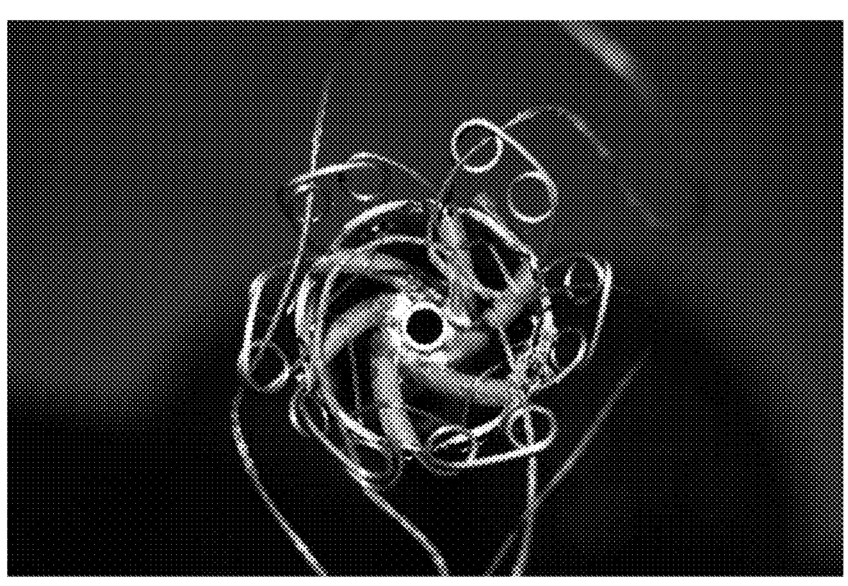
FIGS. 16A-16C are images from left to right which show the deployment stages of one insertion mechanism used in deploying a DCCD.
Figure 16B:
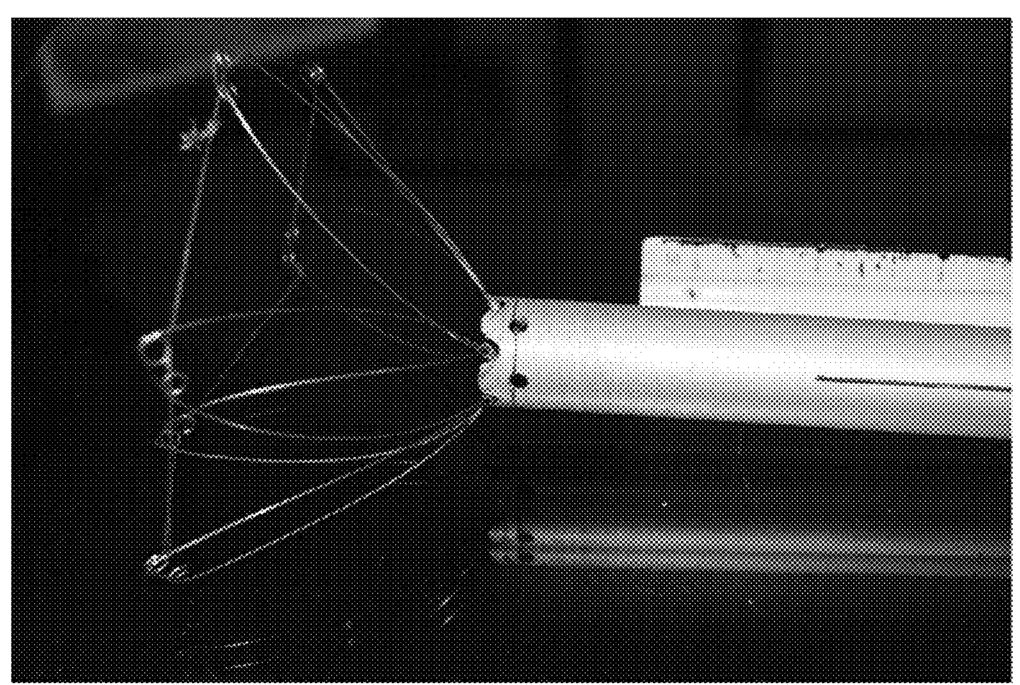
Figure 16C:
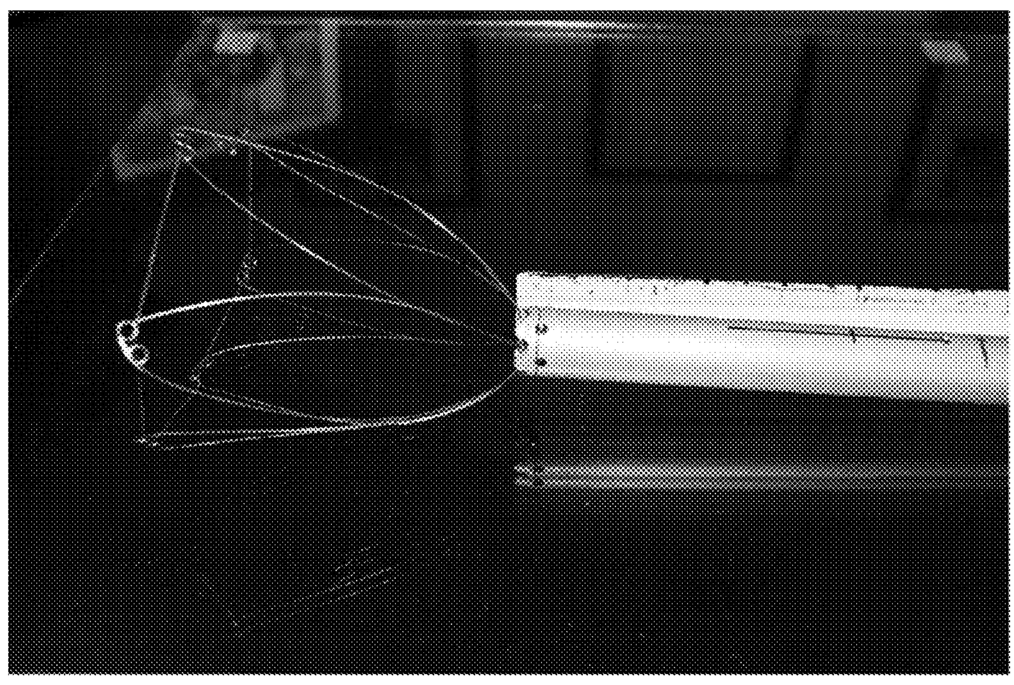

FIGS. 15A-15C are images of the deployment stages of one insertion mechanism used in deploying a DCCD. FIGS. 16A-16C are images from left to right show the deployment stages of one insertion mechanism used in deploying a DCCD. The suture is used to mimic the action obtained when a device is in place.

The present invention includes a device that stabilizes the pericardium to aid in the deployment of the DCCD. Once pericardial access has been obtained the stabilization device keeps the pericardial sac open and allows the user to create separation of the pericardial sac from the apex of the heart. Separation may be necessary to allow space for the deployment of the device. Stabilization of the pericardial sac may be obtained by the following methods. 1) An insertion tube with a flared end that can be placed inside the opening of the pericardium, with or without suturing. 2) An insertion tube with retractable wire loops that when deployed flare outward and slide between the heart wall and pericardium. The wires are stiff enough that when the insertion tube is pulled away from the heart the wire loops lift the pericardium from the surface of the heart. The insertion tube may be separate from the pericardial stabilizer or the insertion tube may contain the pericardial stabilizer.

FIGS. 17A-17D are images of the pericardial stabilizer. FIG. 17A is an image of a side view of the pericardial stabilizer with nitinol wire loops retracted. FIG. 17B is an image of a front view of the pericardial stabilizer with nitinol wire loops retracted. FIG. 17C is an image of a side view of the stabilizer with nitinol loops expanded. FIG. 17D is an image of a front view of the stabilizer with nitinol loops expanded; and FIG. 18A is an image that shows the pericardial stabilizer with two of the six wire loops deployed and FIG. 18B is an image that shows the longitudinal curvature of the pericardial stabilizer.

The present invention provides a device and method for using the device that enable implantation of heart contacting devices in a minimally invasive manner and/or to implant devices around the heart via deployment through a small incision. In one embodiment, the sequence of actions include (1) ejecting—whereby the device is advanced out of the deployment tube; (2) flaring—whereby the device is flared or opened up as it is ejected from the tube so that it begins a deployment path that goes around the heart rather than directly toward the heart; and (3) placing—whereby the device is guided or placed into proper position about the heart.

FIGS. 19A-19C are images that shows one embodiment of the sliding hub of the present invention. FIG. 19A is an image that shows the hub 192 flares the wire 194 as it passes through the hub 192. FIG. 19B is an image that shows the wire 194 is advanced and passes through the hub 192 and is extended and redirected (i.e., flared) beyond the hub 192. FIG. 19C is an image that shows the wire 194 passing through the hub 192 and extending from the deployment tube 196 beyond the hub 192 and the apex 200 of the heart 198 where the wire 194 is redirected and flared.

Figure 20:
FIG. 20 shows an image of the spiral configuration of the passive chamber dividers.
Figure 21A:
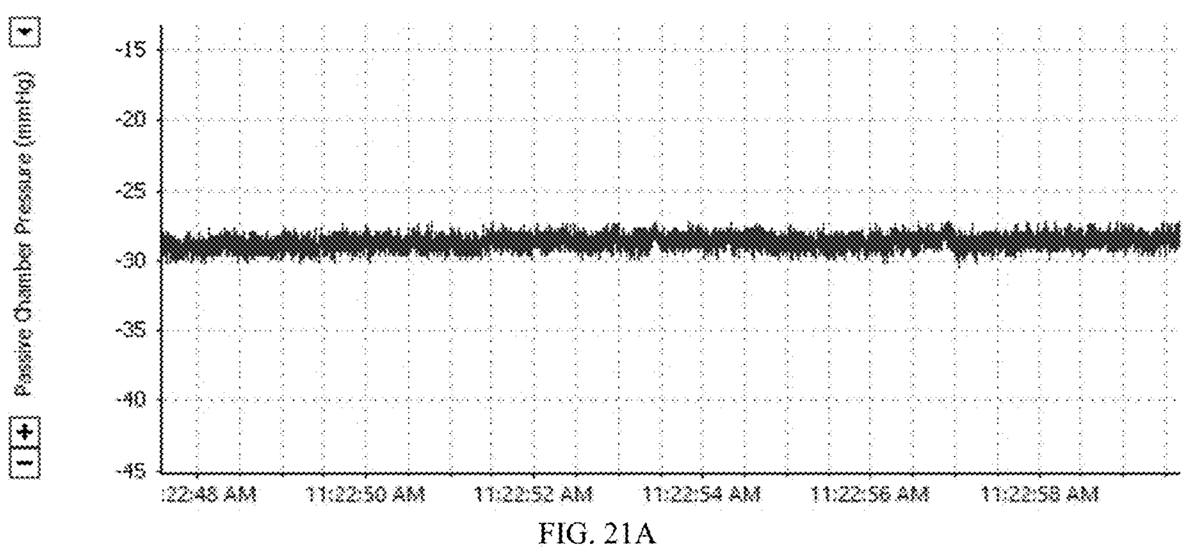
FIGS. 21A-21C are plots of the pressure inside the device as a function of time and operation.
Figures 21B, 21C:
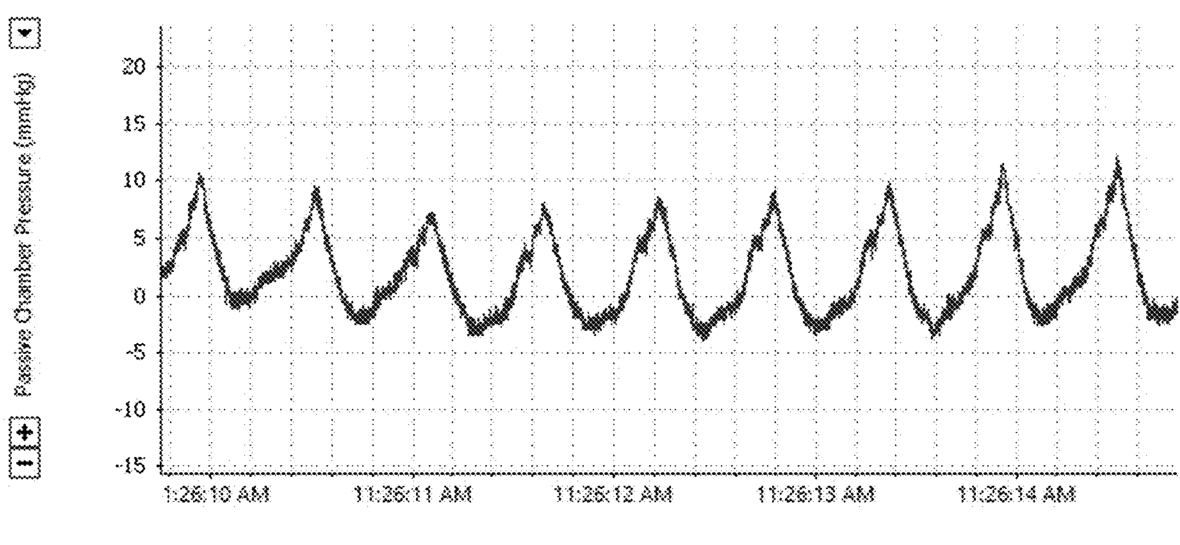

FIG. 20 shows an image of the spiral configuration of the passive chamber dividers. The passive chamber dividers may be positioned between the inner membrane and the connecting membrane, the connecting membrane and the outer membrane or both. The size, shape and placement of the slots in the passive chamber dividers may be configured as necessary to allow the desired flow. After initial insertion, the passive chambers may be empty or have minimal volume of fluid therein resulting in a pressure wave line resembling a flat line (FIG. 21A), perhaps with some noise. Once the device is positioned around the heart, fluid may be slowly added while monitoring pressure inside the passive chambers. Once the passive chamber pressure reflects natural contractions of the heart (FIG. 21B), the infusion of fluid onto the passive chambers may be stopped.

The performance of the device can be monitored by looking at the passive fluid pressure waveform. Passive chambers pressure wave line may be used to monitor performance of the device while in operation. Since the passive chamber is positioned between the heart and the active chambers of the device, the pressure inside the passive chambers reflects both the movement of the heart muscle and the periodic expansion and collapse of the active chambers. During systole, the heart muscle is contracting and moves towards the center of the device and therefore "away" from the inner surface of the passive chambers. Due to its intrinsic pneumatic lock between the surface of the heart and the inner surface of the passive chamber, the heart muscle pulls the inner surface of the passive chamber along causing a drop in the pressure inside thereof. Conversely, active inflation of the active chamber causes a compression of the passive chamber and therefore an increase in pressure inside thereof. Monitoring passive chamber pressure allows a determination of the interaction of these two events, namely contraction of the cardiac muscle and expansion of the active chambers. It is desirable to expand the active chambers more rapidly than the heart muscle contracts—so as to maintain a positive pressure in the passive chambers for as much or a systolic duration as possible—see an example in FIG. 21C. Lack of desired positive pressure level in the passive chamber may be used as an indicator of a need for adjustment in the device operation—such as a change in timing or supplied pressure to the active chambers. During diastole, the pressure in the passive chamber may be maintained at a negative level via applying vacuum to the active chamber—and therefore assisting the heart muscle in expanding to accumulate a greater blood volume prior to the next ejection. The device operation may be adjusted using the passive chamber pressure to accomplish a desired level of negative pressure in the passive chambers. Passive chamber pressure may also be used for monitoring safety and consistency of operation. In embodiments, monitoring for a slow decay in end inflation pressure may be used in one example as an indication of a leak in the active chamber causing less gas to be available to expand the active chamber during the systolic contraction of the heart.

Figure 22:
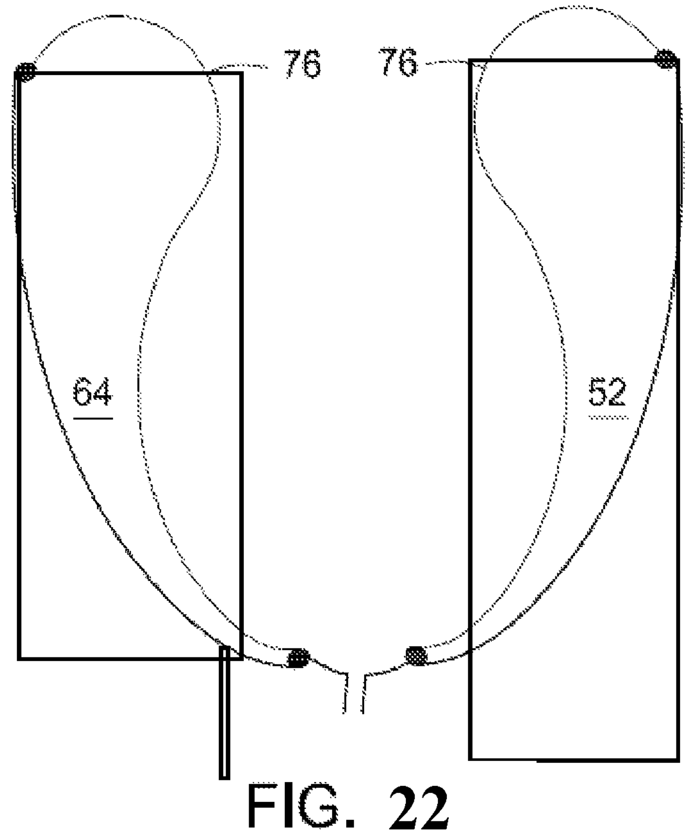
FIG. 22 is a schematic diagram of the long-section of a device in the pressurized state according to one embodiment of the present invention without a heart inside.

FIG. 22 illustrates a vertical cross section of one embodiment of the device of the present invention in the inflated state. Device includes chambers 52 and 64 in the inflated states. The interior surface 76 of the chambers 52-64 that are on the outer boundary form a shape that is similar to the end diastolic shape of the heart. The interior surface 76 has folds and crenulations such that when inflated the chambers 52-64 mostly expand inward to contact the epicardium of the heart (not shown).

To facilitate continuous or intermittent monitoring of the passive chambers pressure, a dedicated separate channel or lumen for infusing of fluid and monitoring fluid pressure in the passive chambers may be provided. Such lumen may be positioned along the length of the main pneumatic pumping line and a pressure sensor may be coupled to this lumen inside the driver of the device. Alternatively, a pressure sensor may be incorporated into the device itself and an electrical wire or wireless communication may be provided to connect the sensor to the driver. In addition this communication may be wireless and transmit the signal through form the inside of the body to a receiver on the surface of the patient or some distance away from the patient.

The present invention aids in deploying and placing properly the device about the heart in that the device opens up as it is ejected from the tube, i.e., the device leaves the tube in a way that advances it toward proper placement, then proper placement is more assured, while also reducing the possibility of heart trauma from device-heart impact. The present invention includes numerous mechanisms to enable appropriate device flare during deployment. In one embodiment, the device is advanced along flared guide-wires about the heart to provide proper placement of the device around the heart. In this embodiment for flaring, multiple guide-wires are placed (individually or simultaneously) firstly along the path that device is intended to travel—i.e., a path that goes from the deployment tube to around the heart. Loops or similar sliding attachment for the device contact the guide-wires so that the device is deployed along a path that goes from the deployment tube to around the heart.

In another embodiment the device uses a flaring deployment jig. In this embodiment for flaring, there is a jig type instrument that aids in surgery or in placement of a device, yet is removed after the device is placed. The deployment jig is part of the deployment tube or can be inserted through the deployment tube. Hence consider a jig that is attached to the device with the jig being constructed so that it flares as it is advanced, thus flaring the device as the device goes with the jig when ejected from the tube.

The present invention also provides an intrinsic device flaring framework. In this embodiment for flaring, there are elements within the device itself that act to flare the device as it is injected. For instance, the device includes compressed spring-like filaments in the leading edge of the device that act to expand the device as it exits the tube and will flare the device as it is deployed.

In addition to the above mechanisms for flaring the device as it is deployed from a tube, the present application includes three additional embodiments illustrating the mechanisms to enable flare of the guide wires: the exit flair embodiment, the jig structure embodiment and/or the device framework embodiment. Basically, any one of the following mechanisms can be used as a method to achieve the above mechanisms.

The exit flair embodiment includes a component near the tube opening that redirects the wires, jig structure, and/or framework radially away from the tube axis. A component including a small exit flare in the deployment tube is one such mechanism that will redirect the guides, jig, or device toward flaring appropriately.

The jig structure embodiment includes a twisting member within the deployment tube that induces a tangential ejection of the wires, jig, or device. Given that a tangent to the tube circumference will produce radial displacement with circumferential displacement, a tangential exit will achieve flare.

The device framework embodiment includes a rolling action on ejection. The guide, jig, or device is inverted in the tube with distal end in the tube being the most proximal after deployment, such that the proximal part is placed firstly at the exit of the tube and the rest of the apparatus (guide, jig, and/or device), when it goes around the placed part it is displaced radially thus achieving flare.

Another aspect of placement of such cardiac contacting devices in a minimally invasive manner is stabilization of the pericardial sac. The above mechanisms are also novel and useful for making a flared surgical jig to be inserted in the pericardial sac to stabilize the edges of the hole in the sac and pull the sac away from the heart to make room for the device to be implanted.

Another embodiment is a device that uses the exit flair embodiment above and the jig structure embodiment above together (i.e., an embodiment that induces a device ejection with both a radial component and a tangential component). In this embodiment, there is a wire framework that provides structural support for the device and the wire framework is used to guide the flaring part for deployment. The wires of the framework pass through a hub that is flared so to match the geometry at the apex of the heart. The wire guides in the hub are oriented so that when the wires are advanced through the hub they go from being aligned with the tube axis to being flared or redirected to go tangent to the apex of the heart. Although it is possible and novel to induce such flaring with only radial displacement as the wire is advanced axially, the curvature of the wire bend can be made more gentle if the wire goes circumferentially as it moves axially and radially. A lower curvature of the wire is sometimes advantageous for minimizing friction and the forces needed to overcome bending resistance.

The present invention provides a heart contact device using a flared deployment device and method. More specifically the present invention provides flaring devices and methods each of which can be used in whole or in part or combined to achieve flared deployment. Additionally, mechanisms can be used to construct a flared surgical jig that permits access to the pericardial space and stabilizes the edges of the hole in the pericardial sac so that the edges do not catch on the device as it is deployed. One specific embodiment includes a wire frame passing through a hub with wire guides that has been conceived and tested extensively.

The geometry of the aforementioned deployment tube and pericardial stabilizer may be cylindrical or elliptical and may have some curvature in the longitudinal direction to allow for better access to the apex of the heart (Geometry of deployment system).

The present invention also includes a device having one or more retractable members extending retractably from the housing, wherein the one or more retractable members are adapted to fit a direct cardiac compression device and the one or more retractable members can be extended to contact the one or more pockets of the direct cardiac compression device to position the direct cardiac compression device about a heart. The one or more retractable members induce flaring to allow the positioning of the DCCD about the apex of a heart. The retractable members may be made of a metal, a nonmetal, a plastic, a polymer, a composite, an alloy, or a combination thereof. The retractable members may have a cross section being oval, circular, rectangular, square, triangular, flat, polygonal or a combination thereof. In addition, the cross section, diameter, and/or composition may be different at different locations in the retractable member and may differ from each retractable member independently. The retractable members may have a curve or a bend or other shape if so desired. In some of the embodiments, a first retractable member may be connected to one or more adjacent retractable members to form a frame. The adjacent retractable members may connect to form a loop, an arch, a triangular connection, an oval, a square, a rectangle or other complex shape.

The incidence of infection associated with medical device implantation is often life threatening, e.g., entercoccus, pseudomonas auerignosa, staphylococcus, and staphylococcus epidermis infections. The present invention may include bioactive layers or coatings to prevent or reduce infections. For example, bioactive agents may be implanted, coated or disseminated from the present invention and include antimicrobials; antibiotics; antimitotics; antiproliferatives; antisecretory agents; non-steroidal anti-inflammatory drugs; immunosuppressive agents; antipolymerases; antiviral agents; antibody targeted therapy agents; prodrugs; free radical scavengers; antioxidants; biologic agents; or combinations thereof. Antimicrobial agents include but are not limited to benzalkoniumchloride, chlorhexidine dihydrochloride, dodecarbonium chloride, and silver sufadiazine. Generally, the amount of antimicrobial agent required depends upon the agent; however, concentrations may range from 0.0001% to 5.0%.

In addition, some embodiments of the present invention may have leads, electrodes or electrical connections incorporated into the device. When present, they may be made from noble metals (e.g., gold, platinum, rhodium, and their alloys) or stainless steel. In addition, ordinary pacemaker leads and defibrillation leads could be also incorporated into the present invention to provide cardiac pacing or defibrillation.

Although the present invention and its advantages have been described in detail, it should be understood that various changes, substitutions and alterations can be made herein without departing from the spirit and scope of the invention as defined by the following claims.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations can be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method to improve diastolic recoil of a heart using a direct cardiac contact compression device comprising the steps of:

providing a direct cardiac compression device, wherein the direct cardiac compression device comprises an inner passive chambers, and a passive port for depositing a passive fluid in the inner passive chambers, wherein the inner passive chambers conform to the end-diastolic shape of the heart; an outer active chambers, and an active fluid disposed in the outer active chambers; an input connection in fluid communication with the outer active chambers to ingress the active fluid into the outer active chambers, and an output connection in fluid communication with the outer active chambers to egress the fluid from the outer active chambers, wherein the active fluid presses on the inner passive chambers to compress the heart;

implanting the direct cardiac compression device around a heart;

filling the inner passive chambers with passive fluid to cause the inner passive chambers to fit to the heart while not impeding heart function or constraining the heart when the direct cardiac contact compression device is inactive, periodically pressurizing the outer active chambers in synchrony with heart contraction to expand the outer active chambers, thereby applying force to the inner passive chambers to compress the heart; and periodically depressurizing the outer active chambers during recoil to contract the inner passive chambers and move the inner passive chambers away from the heart.

2. The method of claim 1, further comprising the step of connecting a pneumatic driver to the input connection and the output connection to pressurize the outer active chambers to compress the heart and depressurize the outer active chambers to aid in filling the heart.

3. The method of claim 1, further comprising a step of using the passive port for adjusting a volume of the passive fluid.

4. The method of claim 1, wherein the passive fluid is a liquid, a gas, a gel, or a polymer.

5. The method of claim 1, wherein the passive fluid is saline.

6. The method of claim 1, wherein the inner passive chambers are contoured to surround the heart operable to actively promote a contraction strain pattern characterized by non-inversion or lack of gross perturbation of the curvature on a diseased or damaged myocardium that promotes beneficial growth and remodeling of the myocardium.

7. The method of claim 1, further comprising a shell surrounding the outer member.

8. The method of claim 1, further comprising one or more components designed to provide adjustable passive support, active assist, or a combination of active assist and passive support to a damaged or diseased heart.

9. The method of claim 1, wherein the inner passive chambers are adapted to form a pneumatic lock with the heart surface.

10. The method of claim 1, further comprising one or more structural elements disposed about the direct cardiac compression device.

11. The method of claim 1, wherein the input connection and the output connection are a single connection.

12. The method of claim 1, wherein the inner passive chambers comprising an inner membrane adapted to surround the heart, a connecting membrane in communication with the inner membrane, one or more passive dividers located between the inner membrane and the connecting membrane to form inner passive chambers.

13. The method of claim 12, wherein the inner passive chambers further comprising one or more additional inner passive dividers positioned between the inner passive membrane and the connecting membrane to form 2 or more inner passive chambers.

14. The method of claim 12, wherein the passive dividers between the inner membrane and the connecting membrane are a series of clock-wise spiral lines when looking down to a location of an apex of the heart, thereby complementing a strain pattern of a muscle of the heart by allowing the apex of the heart to twist during heart compression.

15. The method of claim 1, further comprising a step of monitoring device performance using a pressure signal of the passive fluid.

16. The method of claim 15, further comprising a step of adjusting timing of pressurizing or depressurizing the outer active chambers or adjusting supplied pressure for pressurizing the active chambers in response to monitoring device performance using the pressure signal of the passive fluid.

* * * * *